US009152765B2

(12) United States Patent
Gilham et al.

(10) Patent No.: US 9,152,765 B2
(45) Date of Patent: Oct. 6, 2015

(54) MULTI-DISPLAY BEDSIDE MONITORING SYSTEM

(71) Applicant: Spacelabs Healthcare, Snoqualmie, WA (US)

(72) Inventors: Jeffrey Jay Gilham, Sammamish, WA (US); Patrick Jensen, Sammamish, WA (US); Michael Brendel, Issaquah, WA (US); Katherine Stankus, Woodinville, WA (US)

(73) Assignee: Spacelabs Healthcare LLC, Snoqualmie, WA (US)

( * ) Notice: Subject to any disclaimer, the term of this patent is extended or adjusted under 35 U.S.C. 154(b) by 0 days.

(21) Appl. No.: 14/165,193

(22) Filed: Jan. 27, 2014

(65) Prior Publication Data

US 2014/0203937 A1    Jul. 24, 2014

Related U.S. Application Data

(63) Continuation of application No. 13/052,883, filed on Mar. 21, 2011, now Pat. No. 8,674,837.

(60) Provisional application No. 61/315,967, filed on Mar. 21, 2010.

(51) Int. Cl.
*G08B 23/00* (2006.01)
*G06F 19/00* (2011.01)
(Continued)

(52) U.S. Cl.
CPC .............. *G06F 19/3406* (2013.01); *A61B 5/002* (2013.01); *G06F 3/1438* (2013.01); *G06F 19/322* (2013.01); *G06F 19/345* (2013.01); *G06F 19/3487* (2013.01); *G09G 2380/08* (2013.01)

(58) Field of Classification Search
CPC .............. G06F 19/3406; G06F 19/322; G06F 2380/08
USPC .......... 340/573.1, 573.4, 691.1, 540, 541, 3.2; 600/324, 347, 384, 509, 515
See application file for complete search history.

(56) References Cited

U.S. PATENT DOCUMENTS 2,912,858 A    11/1959   Fuller
3,517,639 A     6/1970   Whitsel
(Continued)

FOREIGN PATENT DOCUMENTS

CN      1688256     10/2005
CN    101194278      6/2008
(Continued)

OTHER PUBLICATIONS

Chinese Office Action, Patent Application No. 201180025170X, Issued Apr. 21, 2014, First OA.
(Continued)

*Primary Examiner* — Tai T Nguyen
(74) *Attorney, Agent, or Firm* — Novel IP

(57) ABSTRACT

The present specification discloses systems and methods for patient monitoring using a multitude of display regions, at least two of which have the capability to simultaneously display real time patient waveforms and vital statistics as well as provide display for local and remote software applications. In one example, a primary display shows real time patient waveforms and vital statistics while a customizable secondary display shows trends, cumulative data, laboratory and radiology reports, protocols, and similar clinical information. Additionally, the secondary display can launch local and remote applications such as entertainment software, Internet and email programs, patient education software, and video conferencing applications. The dual display allows caregivers to simultaneously view real time patient vitals and aggregated data or therapy protocols, thereby increasing hospital personnel efficiency and improving treatment, while not compromising the display of critical alarms or other data.

18 Claims, 11 Drawing Sheets

(51) Int. Cl.
  *G06F 3/14* (2006.01)
  *A61B 5/00* (2006.01)

(56) References Cited

U.S. PATENT DOCUMENTS

| | | |
|---|---|---|
| 3,618,592 A | 11/1971 | Stewart |
| 3,673,863 A | 7/1972 | Spacek |
| 3,938,551 A | 2/1976 | Henkin |
| 4,064,826 A | 12/1977 | Pauli |
| 4,148,312 A | 4/1979 | Bird |
| 4,167,115 A | 9/1979 | Stoever |
| 4,513,294 A | 4/1985 | Anderson |
| 4,557,216 A | 12/1985 | Demyon |
| 4,625,731 A | 12/1986 | Quedens |
| 4,630,486 A | 12/1986 | Miles |
| 4,697,450 A | 10/1987 | Bachman |
| 4,869,253 A | 9/1989 | Craig |
| 4,903,222 A | 2/1990 | Carter |
| 4,944,305 A | 7/1990 | Takatsu |
| 4,991,576 A | 2/1991 | Henkin |
| 5,087,906 A | 2/1992 | Eaton |
| 5,101,851 A | 4/1992 | Abadi |
| 5,144,898 A | 9/1992 | Posly |
| 5,197,480 A | 3/1993 | Gebhardt |
| 5,213,108 A | 5/1993 | Bredesen |
| 5,231,981 A | 8/1993 | Schreiber |
| 5,233,975 A | 8/1993 | Choate |
| 5,262,944 A | 11/1993 | Weisner |
| 5,291,182 A | 3/1994 | Wiseman |
| 5,311,908 A | 5/1994 | Barone |
| 5,319,363 A | 6/1994 | Welch |
| 5,322,069 A | 6/1994 | Gallant |
| 5,331,549 A | 7/1994 | Crawford, Jr. |
| 5,339,826 A | 8/1994 | Schmidt |
| 5,348,008 A | 9/1994 | Bornn |
| 5,373,746 A | 12/1994 | Bloss |
| 5,419,332 A | 5/1995 | Sabbah |
| 5,438,983 A | 8/1995 | Falcone |
| 5,467,954 A | 11/1995 | Wekell |
| 5,473,536 A | 12/1995 | Wimmer |
| 5,482,050 A | 1/1996 | Smokoff |
| 5,497,766 A | 3/1996 | Foster |
| 5,502,853 A | 4/1996 | Singleton |
| 5,515,083 A | 5/1996 | Casebolt |
| 5,553,296 A | 9/1996 | Forrest |
| 5,558,418 A | 9/1996 | Lambright |
| 5,563,495 A | 10/1996 | Tomiyori |
| 5,584,291 A | 12/1996 | Vapola |
| 5,586,909 A | 12/1996 | Saba |
| 5,633,457 A | 5/1997 | Kilar |
| 5,682,526 A | 10/1997 | Smokoff |
| 5,687,717 A | 11/1997 | Halpern |
| 5,692,494 A | 12/1997 | Pernetti |
| 5,715,813 A | 2/1998 | Guevrekian |
| 5,718,235 A | 2/1998 | Golosarsky |
| 5,724,025 A | 3/1998 | Tavori |
| 5,724,985 A | 3/1998 | Snell |
| 5,749,367 A | 5/1998 | Gamlyn |
| 5,765,842 A | 6/1998 | Phaneuf |
| 5,779,305 A | 7/1998 | Hocking |
| 5,787,298 A | 7/1998 | Broedner |
| 5,800,360 A | 9/1998 | Kisner |
| 5,819,741 A | 10/1998 | Karlsson |
| 5,855,550 A | 1/1999 | Lai |
| 5,868,133 A | 2/1999 | DeVries |
| 5,904,328 A | 5/1999 | Leveridge |
| 5,956,013 A | 9/1999 | Raj |
| 5,975,081 A | 11/1999 | Hood |
| 6,005,767 A | 12/1999 | Ku |
| 6,024,089 A | 2/2000 | Wallace |
| 6,048,044 A | 4/2000 | Biggel |
| 6,050,940 A | 4/2000 | Braun |
| 6,063,028 A | 5/2000 | Luciano |
| 6,096,025 A | 8/2000 | Borders |
| 6,099,093 A | 8/2000 | Spence |
| 6,131,571 A | 10/2000 | Lampotang |
| 6,134,537 A | 10/2000 | Pao |
| 6,146,523 A | 11/2000 | Kenley |
| 6,155,255 A | 12/2000 | Lambert |
| 6,322,502 B1 | 11/2001 | Schoenberg |
| 6,338,823 B1 | 1/2002 | Furukawa |
| 6,339,732 B1 | 1/2002 | Phoon |
| 6,347,310 B1 | 2/2002 | Passera |
| 6,383,136 B1 | 5/2002 | Jordan |
| 6,396,583 B1 | 5/2002 | Clare |
| 6,424,860 B1 | 7/2002 | Karlsson |
| 6,435,690 B1 | 8/2002 | Till |
| 6,443,889 B1 | 9/2002 | Groth |
| D467,001 S | 12/2002 | Buczek |
| 6,488,029 B1 | 12/2002 | Hood |
| 6,536,430 B1 | 3/2003 | Smith |
| 6,554,238 B1 | 4/2003 | Hibberd |
| 6,571,227 B1 | 5/2003 | Agrafiotis |
| 6,571,792 B1 | 6/2003 | Hendrickson |
| 6,591,694 B2 | 7/2003 | Tsai |
| 6,600,662 B1 | 7/2003 | Emmert |
| 6,647,341 B1 | 11/2003 | Golub |
| 6,650,779 B2 | 11/2003 | Vachtrsvanos |
| 6,674,837 B1 | 1/2004 | Taskar |
| 6,692,258 B1 | 2/2004 | Kurzweil |
| 6,692,436 B1 | 2/2004 | Bluth |
| 6,699,187 B2 | 3/2004 | Webb |
| 6,702,754 B2 | 3/2004 | Ogura |
| 6,715,722 B2 | 4/2004 | Roberts |
| 6,735,648 B2 | 5/2004 | Onishi |
| 6,771,172 B1 | 8/2004 | Robinson |
| 6,804,656 B1 | 10/2004 | Rosenfeld |
| 6,824,539 B2 | 11/2004 | Novak |
| 6,829,501 B2 | 12/2004 | Nielsen |
| 6,931,795 B1 | 8/2005 | Baloga |
| 6,933,931 B2 | 8/2005 | Lubarsky, Jr. |
| 6,985,762 B2 | 1/2006 | Brashears |
| 7,006,865 B1* | 2/2006 | Cohen et al. ............ 607/5 |
| 7,013,833 B2 | 3/2006 | Lemberger |
| 7,024,569 B1 | 4/2006 | Wright |
| 7,031,857 B2 | 4/2006 | Tarassenko |
| 7,038,588 B2 | 5/2006 | Boone |
| 7,076,435 B1 | 7/2006 | McKeag |
| 7,081,091 B2 | 7/2006 | Merrett |
| RE39,233 E | 8/2006 | McGrath |
| 7,096,864 B1 | 8/2006 | Mayer |
| 7,111,852 B2 | 9/2006 | Woods |
| 7,117,438 B2 | 10/2006 | Wallace |
| 7,137,951 B2 | 11/2006 | Pilarski |
| 7,193,233 B2 | 3/2007 | Smith |
| 7,223,007 B1 | 5/2007 | Fredley |
| 7,256,708 B2 | 8/2007 | Rosenfeld |
| 7,267,666 B1 | 9/2007 | Duchon |
| 7,282,029 B1 | 10/2007 | Poulsen |
| 7,315,825 B2 | 1/2008 | Rosenfeld |
| 7,336,980 B1 | 2/2008 | Kaikuranta |
| 7,360,454 B2 | 4/2008 | Kawashima |
| 7,371,214 B2 | 5/2008 | Kouchi |
| 7,386,340 B2 | 6/2008 | Schlegel |
| 7,468,032 B2 | 12/2008 | Stahmann |
| 7,469,601 B2 | 12/2008 | Sugi |
| D589,959 S | 4/2009 | Han |
| 7,516,924 B2 | 4/2009 | White |
| 7,523,040 B2 | 4/2009 | Kirchhoff |
| 7,529,083 B2 | 5/2009 | Jeong |
| 7,540,187 B1 | 6/2009 | Dillon |
| 7,566,307 B2 | 7/2009 | Inukai |
| 7,621,500 B2 | 11/2009 | Ishizaki |
| 7,751,878 B1 | 7/2010 | Merkle |
| 7,756,722 B2 | 7/2010 | Levine |
| 7,945,452 B2 | 5/2011 | Fathallah |
| 8,027,846 B2* | 9/2011 | Schoenberg et al. ......... 705/2 |
| 8,147,419 B2* | 4/2012 | Krauss et al. ............ 600/529 |
| 8,344,847 B2 | 1/2013 | Moberg |
| 2001/0001179 A1 | 5/2001 | Healy |
| 2001/0018332 A1 | 8/2001 | Lustila |
| 2001/0027791 A1 | 10/2001 | Wallace |
| 2001/0034475 A1 | 10/2001 | Flach |
| 2002/0026941 A1 | 3/2002 | Biondi |

(56) References Cited

U.S. PATENT DOCUMENTS

| | | |
|---|---|---|
| 2002/0032386 A1 | 3/2002 | Sackner |
| 2002/0108011 A1 | 8/2002 | Tanha |
| 2002/0161291 A1 | 10/2002 | Kianl |
| 2002/0193679 A1 | 12/2002 | Malave |
| 2002/0196141 A1* | 12/2002 | Boone et al. ............ 340/540 |
| 2003/0028118 A1 | 2/2003 | Dupree |
| 2003/0029451 A1 | 2/2003 | Blair |
| 2003/0037786 A1 | 2/2003 | Biondi |
| 2003/0076015 A1 | 4/2003 | Ehrenreich |
| 2003/0114836 A1 | 6/2003 | Estes |
| 2003/0117296 A1 | 6/2003 | Seely |
| 2003/0120164 A1 | 6/2003 | Nielsen |
| 2003/0130590 A1 | 7/2003 | Bui |
| 2003/0135087 A1 | 7/2003 | Hickle |
| 2003/0145854 A1 | 8/2003 | Hickle |
| 2003/0171898 A1 | 9/2003 | Tarassenko |
| 2003/0191373 A1 | 10/2003 | Blike |
| 2003/0209246 A1 | 11/2003 | Schroeder |
| 2003/0210780 A1 | 11/2003 | Pratt |
| 2003/0216621 A1 | 11/2003 | Alpert |
| 2003/0231460 A1 | 12/2003 | Moscovitch |
| 2003/0233129 A1 | 12/2003 | Matos |
| 2004/0011938 A1 | 1/2004 | Oddsen |
| 2004/0015079 A1 | 1/2004 | Berger |
| 2004/0021705 A1 | 2/2004 | Baker |
| 2004/0024303 A1 | 2/2004 | Banks |
| 2004/0032426 A1 | 2/2004 | Rutledge |
| 2004/0054261 A1 | 3/2004 | Kamataki |
| 2004/0054295 A1 | 3/2004 | Ramseth |
| 2004/0102687 A1 | 5/2004 | Brashears |
| 2004/0103001 A1 | 5/2004 | Mazar |
| 2004/0116813 A1 | 6/2004 | Selzer |
| 2004/0117209 A1 | 6/2004 | Brown |
| 2004/0118404 A1 | 6/2004 | Wallace |
| 2004/0147818 A1 | 7/2004 | Levy |
| 2004/0153257 A1 | 8/2004 | Munk |
| 2004/0158132 A1 | 8/2004 | Zaleski |
| 2004/0172222 A1 | 9/2004 | Simpson |
| 2004/0186357 A1 | 9/2004 | Soderberg |
| 2004/0221077 A1 | 11/2004 | Yen |
| 2004/0236192 A1 | 11/2004 | NecolaShehada |
| 2004/0249298 A1 | 12/2004 | Selevan |
| 2004/0249673 A1 | 12/2004 | Smith |
| 2005/0005932 A1 | 1/2005 | Berman |
| 2005/0010165 A1 | 1/2005 | Hickle |
| 2005/0033124 A1 | 2/2005 | Kelly |
| 2005/0038332 A1 | 2/2005 | Saidara |
| 2005/0038821 A1 | 2/2005 | Wallen |
| 2005/0054920 A1 | 3/2005 | Washburn |
| 2005/0059924 A1 | 3/2005 | Katz |
| 2005/0065417 A1 | 3/2005 | Ali |
| 2005/0113650 A1 | 5/2005 | Pacione |
| 2005/0124866 A1 | 6/2005 | Elaz |
| 2005/0139213 A1 | 6/2005 | Blike |
| 2005/0146431 A1 | 7/2005 | Hastings |
| 2005/0151640 A1 | 7/2005 | Hastings |
| 2005/0251232 A1 | 11/2005 | Hartley |
| 2006/0004475 A1 | 1/2006 | Brackett |
| 2006/0022096 A1 | 2/2006 | Chan |
| 2006/0042635 A1 | 3/2006 | Niklewski |
| 2006/0058591 A1 | 3/2006 | Garboski |
| 2006/0094970 A1 | 5/2006 | Drew |
| 2006/0155206 A1 | 7/2006 | Lynn |
| 2006/0199618 A1 | 9/2006 | Steer |
| 2006/0226992 A1 | 10/2006 | Al-Ali |
| 2006/0258926 A1 | 11/2006 | Ali |
| 2006/0280621 A1 | 12/2006 | Kinugawa |
| 2007/0007418 A1 | 1/2007 | Lubbers |
| 2007/0028921 A1 | 2/2007 | Banner |
| 2007/0032749 A1 | 2/2007 | Overall |
| 2007/0044578 A1 | 3/2007 | Jones |
| 2007/0051861 A1 | 3/2007 | Teramachi |
| 2007/0060869 A1 | 3/2007 | Tolle |
| 2007/0093784 A1 | 4/2007 | Leonard |
| 2007/0107728 A1 | 5/2007 | Ricciardelli |
| 2007/0120763 A1 | 5/2007 | De |
| 2007/0176931 A1 | 8/2007 | Tivig |
| 2007/0180140 A1 | 8/2007 | Welch |
| 2007/0199388 A1 | 8/2007 | Furkert |
| 2007/0255116 A1 | 11/2007 | Mehta |
| 2007/0265533 A1 | 11/2007 | Tran |
| 2007/0276277 A1 | 11/2007 | Booth |
| 2008/0033254 A1 | 2/2008 | Kamath |
| 2008/0039701 A1 | 2/2008 | Ali |
| 2008/0051667 A1 | 2/2008 | Goldreich |
| 2008/0154909 A1 | 6/2008 | Dam |
| 2008/0167569 A1 | 7/2008 | Ermes |
| 2008/0170287 A1 | 7/2008 | Champion |
| 2008/0177160 A1 | 7/2008 | Al Ali |
| 2008/0177397 A1 | 7/2008 | Davlin |
| 2008/0221418 A1 | 9/2008 | Al-Ali |
| 2008/0228089 A1 | 9/2008 | Cho |
| 2008/0249376 A1 | 10/2008 | Zaleski |
| 2008/0251003 A1 | 10/2008 | Boston |
| 2008/0271736 A1 | 11/2008 | Leonard |
| 2008/0275309 A1 | 11/2008 | Stivoric |
| 2008/0281168 A1 | 11/2008 | Gibson |
| 2008/0281170 A1 | 11/2008 | Eshelman |
| 2008/0287763 A1 | 11/2008 | Hayter |
| 2008/0294057 A1 | 11/2008 | Parlikar |
| 2008/0310600 A1 | 12/2008 | Clawson |
| 2008/0319331 A1 | 12/2008 | Zizzo |
| 2009/0005703 A1 | 1/2009 | Fasciano |
| 2009/0015116 A1 | 1/2009 | Arceta |
| 2009/0024008 A1 | 1/2009 | Brunner |
| 2009/0054743 A1 | 2/2009 | Stewart |
| 2009/0069642 A1 | 3/2009 | Gao |
| 2009/0076345 A1 | 3/2009 | Manicka |
| 2009/0099480 A1 | 4/2009 | Salgo |
| 2009/0117784 A1 | 5/2009 | Wu |
| 2009/0124239 A1 | 5/2009 | Tsuei |
| 2009/0131805 A1* | 5/2009 | O'Brien et al. ............ 600/485 |
| 2009/0133609 A1 | 5/2009 | Nethken |
| 2009/0149901 A1 | 6/2009 | Jayne |
| 2009/0182204 A1 | 7/2009 | Semler |
| 2009/0192541 A1 | 7/2009 | Ortiz |
| 2009/0193315 A1 | 7/2009 | Gower |
| 2009/0200902 A1 | 8/2009 | McKay |
| 2009/0206713 A1 | 8/2009 | Vilkas |
| 2009/0209849 A1 | 8/2009 | Rowe |
| 2010/0004539 A1 | 1/2010 | Chen |
| 2010/0007588 A1 | 1/2010 | Zygmunt |
| 2010/0056875 A1 | 3/2010 | Schoenberg |
| 2010/0094096 A1 | 4/2010 | Petruzzelli |
| 2010/0137729 A1 | 6/2010 | Pierry |
| 2010/0164452 A1 | 7/2010 | Ruan |
| 2010/0175695 A1 | 7/2010 | Jamison |
| 2010/0179400 A1 | 7/2010 | Brauker |
| 2010/0233891 A1 | 9/2010 | Broeksteeg |
| 2010/0238138 A1 | 9/2010 | Goertz |
| 2010/0261979 A1 | 10/2010 | Kiani |
| 2010/0294405 A1 | 11/2010 | Longinotti-Buitoni |
| 2010/0298656 A1 | 11/2010 | Mccombie |
| 2010/0298718 A1 | 11/2010 | Gilham |
| 2010/0324380 A1 | 12/2010 | Perkins |
| 2010/0324384 A1 | 12/2010 | Moon |
| 2011/0004071 A1 | 1/2011 | Faiola |
| 2011/0088694 A1 | 4/2011 | Tobia |
| 2011/0130798 A1 | 6/2011 | Elghazzawi |
| 2011/0152629 A1 | 6/2011 | Eaton |
| 2011/0164074 A1 | 7/2011 | Frank |
| 2011/0245579 A1 | 10/2011 | Bruggeman |
| 2011/0257489 A1 | 10/2011 | Banet |
| 2011/0279383 A1 | 11/2011 | Wilson |
| 2011/0279958 A1 | 11/2011 | Clark |
| 2012/0030610 A1 | 2/2012 | DiPerna |
| 2012/0075327 A1 | 3/2012 | Mackenzie |
| 2012/0105233 A1 | 5/2012 | Bobey |
| 2012/0127103 A1 | 5/2012 | Qualey |
| 2012/0209984 A1 | 8/2012 | Gonzalez-Banos |

(56) References Cited

U.S. PATENT DOCUMENTS

| | | | |
|---|---|---|---|
| 2012/0232398 | A1 | 9/2012 | Roham |
| 2013/0267861 | A1 | 10/2013 | Vassallo |

FOREIGN PATENT DOCUMENTS

| | | | |
|---|---|---|---|
| EP | 0686900 | A2 | 12/1995 |
| EP | 1054338 | | 11/2000 |
| EP | 1852060 | | 11/2007 |
| GB | 2389290 | A | 12/2003 |
| JP | 07163527 | | 6/1995 |
| JP | 2003210422 | | 7/2003 |
| WO | 9415523 | | 7/1994 |
| WO | 9918705 | | 4/1999 |
| WO | 03091841 | | 11/2003 |
| WO | 03102850 | | 12/2003 |
| WO | 2006094055 | A2 | 9/2006 |
| WO | 2010126916 | | 11/2010 |
| WO | 2010126916 | A1 | 11/2010 |
| WO | 2011001302 | A1 | 1/2011 |
| WO | 2011046636 | A1 | 4/2011 |
| WO | 2011047363 | A1 | 4/2011 |
| WO | 2011119512 | A1 | 9/2011 |
| WO | 2012068564 | A2 | 5/2012 |
| WO | 2012068565 | A2 | 5/2012 |
| WO | 2012068567 | | 5/2012 |
| WO | 2012068568 | A2 | 5/2012 |
| WO | 2012083276 | A2 | 6/2012 |
| WO | 2012083281 | A1 | 6/2012 |
| WO | 2012125135 | A1 | 9/2012 |
| WO | 2012128808 | A2 | 9/2012 |
| WO | 2012158720 | A1 | 11/2012 |
| WO | 2013056171 | A2 | 4/2013 |
| WO | 2013173520 | A2 | 11/2013 |
| WO | 2013173521 | A2 | 11/2013 |
| WO | 2014055660 | A1 | 4/2014 |
| WO | 2014194193 | | 12/2014 |

OTHER PUBLICATIONS

Office Action Dated May 31, 2013 for U.S. Appl. No. 13/052,883.
International Search Report for PCT/US2011/029278, Aug. 2, 2011.
International Search Report for PCT/US2013/063087, Mar. 6, 2014.
Supplementary European Search Report, Nov. 25, 2009, Spacelabs Medical, PCT/US2006/007269.
Schoenberg, Roy, MD; Sands, Daniel Z., MD MPH; Safran, Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.
International Search Report for PCT/US06/07269, Aug. 28, 2006.
International Preliminary Report on Patentability, PCT/US2006/007269, Sep. 11, 2007, Spacelabs Medical.
Notice of Allowance dated Oct. 31, 2014 for U.S. Appl. No. 12/114,689.
International Search Report for PCT/US10/32635, Jul. 23, 2010.
Office Action dated Feb. 26, 2015 for U.S. Appl. No. 12/768,714.
Office Action dated Aug. 14, 2014 for U.S. Appl. No. 12/768,714.
Office Action dated Nov. 21, 2013 for U.S. Appl. No. 12/768,714.
Office Action dated Jun. 18, 2012 for U.S. Appl. No. 12/768,714.
Office Action dated Jan. 17, 2013 for U.S. Appl. No. 12/768,714.
International Search Report for PCT/US2011/61557, Apr. 23, 2012.
International Search Report for PCT/US2011/061554, Feb. 14, 2014.
International Search Report for PCT/US2011/061555, Apr. 17, 2012.
International Search Report for PCT/US2011/061558, Aug. 10, 2012.
International Preliminary Report on Patentability for PCT/US2011/061554, Feb. 25, 2014.
IntelliVue Patient Monitor; MP20/30, MP40/50, MP60/70/80/90, Release G.0 with Software Revision G.0x.xx (PHILIPS) Sep. 2008; pp. 4, 10, 19, 20, 46-49, 82, 326, 348, 420, 422, 424, 452; Accessed on Sep. 30, 2013: <http://www.mc.vanderbilt.edu/documents/nursingeducationresources/files/MP20-MP90%20Instructions%20for%20Use%20Manual%20REv_G_0%20%20English%20M8000-9001K.pdf>.
Office Action dated Nov. 12, 2014 for U.S. Appl. No. 13/300,462.
Notice of Allowance dated Jan. 28, 2015 for U.S. Appl. No. 13/300,478.
International Search Report, PCT/US2011/028007, Jul. 11, 2011, International Search Authority.
International Preliminary Report on Patentability, PCT/US2011/028007, Sep. 17, 2013, International Search Authority.
Office Action dated Nov. 21, 2014 for U.S. Appl. No. 13/045,539.
International Preliminary Report on Patentability, PCT/US12/38000, Nov. 13, 2013.
International Search Report for PCT/US12/38000, Oct. 23, 2012.
International Search Report for PCT/US10/34025, Aug. 9, 2010.
Notice of Allowance dated Mar. 13, 2015 for U.S. Appl. No. 12/906,081.
International Search Report for PCT/US2012/060125, Apr. 19, 2013.
International Search Report for PCT/US2010/052977, Mar. 18, 2011.
International Search Report for PCT/US2011/065676, Sep. 20, 2012.
International Search Report for PCT/US2011/065678, Jun. 29, 2012.
International Search Report, PCT/US2011/065685, May 8, 2012, International Search Authority.
International Preliminary Report on Patentability, PCT/US2011/065678, Jun. 18, 2013, International Search Authority.
International Preliminary Report on Patentability, PCT/US2011/065685, Jun. 18, 2013.
Office Action dated Sep. 22, 2014 for U.S. Appl. No. 13/329,186.
Notice of Allowance dated Jan. 8, 2015 for U.S. Appl. No. 13/329,259.
International Search Report for PCT/US2014/040225, Nov. 5, 2014.
International Search Report for PCT/US2013/041246, Dec. 9, 2013.
International Search Report for PCT/US2013/041247, Jan. 10, 2014.

* cited by examiner

MULTI-DISPLAY BEDSIDE MONITORING SYSTEM

CROSS-REFERENCE

The present specification is a continuation of U.S. patent application Ser. No. 13/052,883, issued as U.S. Pat. No. 8,674,738, which relies on U.S. Patent Provisional No. 61/315,967, filed on Mar. 21, 2010, for priority and is incorporated herein by reference.

FIELD OF INVENTION

The present specification relates to patient monitoring systems. More particularly, the present specification relates to a system and method of patient monitoring using dual display bedside monitors that are connected to a hospital information system and have the capability to simultaneously display real time patient waveforms and vital statistics as well as provide display for local and remote software applications.

BACKGROUND OF THE INVENTION

Conventional patient bedside monitors are connected to various vital statistics measuring/monitoring devices and display the real time patient vital statistics, such as pulse rate and blood pressure, among other variables, continuously. Usually, the displayed vital statistics are not recorded in the monitor, and hence, once they disappear from a display, the information is not further cached, buffered, or otherwise stored, and therefore lost. In cases where the monitor records displayed information and presents it in the form of patient health trends, the display of real time vital statistics is obscured.

In a hospital environment, patient specific information such as blood test reports and X-ray reports, among other data, are generated at sites remote to the patient bedside. Such information is usually stored in the hospital information system and may be accessed by caregivers as and when required from a central server. The caregivers may be required to carry the information in paper form in order to study/compare it in context with the real time patient vital statistics. As the volume of paper being carried by the caregiver increases, the chances of delay in diagnosis/treatment due to delay in finding a relevant piece of information, increase as well. Also, some piece of patient information may not be available with the caregiver at any given time and may cause a delay or an error in diagnosis and treatment.

Hence, there is need for a patient bedside monitor which is capable of connecting with the hospital information system and displaying all the information related to a specific patient. There is need for a bedside monitor which can display all the patient related information available with the hospital at the same time and without obscuring the real time display of the patient's vital statistics. There is need for a smart bedside monitor that can provide analyses of the patient's health information over a specified period of time corresponding to any pre-defined criteria set by a caregiver.

Furthermore, there is a need for a multi-purpose display that can be partially under a user's control but not supersede or compromise critical functions, such as the display of key monitored physiological parameters or issuance of alarms in relation to monitored events. The multi-purpose display enables a single physical display unit to perform multiple functions, thereby avoiding taking up excessive hospital room space by additional display units, while not undermining, sacrificing, or compromising the core function of a physiological display.

SUMMARY OF THE INVENTION

The present specification is directed toward a dual display bedside monitor that is connected to a hospital information system and has the capability to simultaneously display real time patient waveforms and vital statistics as well as provide a display for local and remote software applications.

In one embodiment, the present specification is directed toward a system for measuring and displaying a multitude of patient physiological parameters using dual displays at the bedside comprising the following: a patient monitoring system containing various ports for connection of a multitude of physiological parameter measuring devices; a dual display device connected to said patient monitoring system; a database in communication with said patient monitoring system; a hospital information system in communication with said dual display device and said database; and, a plurality of laboratories in communication with said hospital information system.

In one embodiment, the physiological parameter measuring devices include ECG, IBP, NIBP, $SpO_2$, cardiac output, temperature, capnography, BIS, $SvO_2$, and EEG measuring devices.

In one embodiment, the dual display device comprises a separate primary display and a separate secondary display. In another embodiment, the dual display device comprises a single display with a first screen area dedicated as a primary display and a second screen area dedicated as a secondary display. In yet another embodiment, the dual display device comprises a separate primary display and a tablet PC that acts as a separate secondary display which connects to the patient bedside monitor.

In various embodiments, the separate primary display, separate secondary display, and single display each measure 19 inches diagonally. In other embodiments, the displays each measure 22 inches diagonally. In another embodiment, the separate primary display measures 19 inches diagonally and the separate secondary display measures 22 inches diagonally. In yet another embodiment, the separate primary display measures 22 inches diagonally and the separate secondary display measures 19 inches diagonally.

In various embodiments, the separate primary display, separate secondary display, and single display each have a screen resolution of 1280×1024 pixels. In another embodiment, the separate primary display has a screen resolution of 1024×768 pixels and separate secondary display has a screen resolution of 1280×1024 pixels.

In one embodiment, the primary display continuously renders measured real time patient waveforms and vital signs and the secondary display renders user specified applications. In another embodiment, both the primary and secondary displays are capable of rendering user specified applications but the primary display is reserved for real time monitoring when an event of significance occurs. In another embodiment, both the primary and secondary displays are capable of rendering real time monitoring information during an event of significance.

In one embodiment, in which there is only a single display, the entirety of the single display is capable of rendering user specified applications. In one embodiment, the user specified applications are minimized during an event of significance, allowing real time monitoring information to be displayed. In another embodiment, a message is displayed on top of the user specified applications, and said user specified applications are minimized if said message is not acknowledged within a predetermined period of time, allowing real time monitoring information to be displayed. In yet another embodiment, the user specified applications are minimized after a predetermined period of inactivity, allowing real time monitoring information to be displayed. In various embodiments, the predetermined period of time is 1, 3, 5, or 15 minutes.

In one embodiment, an event of significance refers to a plurality of caregiver-predetermined states or scenarios, or occurs whenever a set of values falls outside caregiver-predetermined thresholds or rules. In one embodiment, events of significance are managed by a clinical context manager. In one embodiment, the clinical context manager, based upon the current clinical context, launches local or remote applications.

In one embodiment, the primary display further renders alarm state and technical and medical status information. In one embodiment, the user specified applications rendered by the secondary display comprises information aggregated from said database and said hospital information system. The user specified applications rendered by the secondary display can also comprise local and remote software applications. A plurality of user defined widgets is used to access aggregate data or launch applications. The local and remote software applications can comprise one or more of the following: entertainment software, internet or other network connectivity, patient education software, email applications, and video conferencing applications. In one embodiment, the local software applications are hosted on the dual display bedside monitor. In one embodiment, the remote software applications are hosted on a remote computing device such as a separate bedside monitor, a central workstation, or a physician's office PC.

In one embodiment, the dual display device runs in patient mode when a caregiver is not present and runs in caregiver mode when a caregiver is using the system. Clinical settings are inaccessible while the system is in patient mode. The caregiver has access to clinical settings while the system is in caregiver mode. A caregiver is able to gain access to caregiver mode by entering a credential or password, or by swiping an RFID badge.

In one embodiment, the database comprises at least one storage memory that resides locally within said dual display device and at least one storage memory that resides externally from said dual display device.

In one embodiment, the present specification is directed toward a method for measuring and displaying a multitude of patient physiological parameters using dual displays at the bedside comprising the following steps: measuring a plurality of patient physiological parameters using a multitude of measuring devices attached to a bedside patient monitoring system; transmitting measured data from said patient monitoring system to connected dual display device; displaying real time information on a primary display of said dual display device; additionally transmitting said data from patient monitoring system to a connected database for storing; transmitting some or all of stored data from said database to a hospital information system; transmitting additional patient information gathered from a plurality of laboratories to said hospital information system; and, displaying remote software applications and information aggregated from said database and hospital information system on a secondary display of said dual display device.

In one embodiment, real time patient vital statistics, alarm states, and technical and medical status are continuously displayed on said primary display of said dual display device. Some or all of the real time data is concurrently stored on the database. The stored data is transmitted from the database to the hospital information system via standard output formats such as HL7, Medibus. In one embodiment, the stored data is transmitted from the database to the hospital information system at predetermined intervals. In one embodiment, the stored data is accessed via customizable queries to the database.

In another embodiment, the present specification discloses a display system for displaying critical patient data and/or non-critical data, comprising: a plurality of ports configured to connect said display system to a plurality of physiological parameter measuring devices; at least one port configured to connect said display system to at least one network; a display screen comprising a plurality of pixels divided into a first display region and a second display region, wherein said first display region displays data from a first video buffer and wherein said second display region displays data from a second video buffer; and a controller for directing non-critical data to said first video buffer and said second video buffer, wherein, in response to a triggering event, said controller stops directing non-critical data to the first video buffer and directs critical patient data to the first video buffer.

Optionally, the triggering event is at least one of an alarm, a physiological parameter exceeding a predefined threshold, a passage of time, a physiological parameter falling below a predefined threshold, or a detected disconnection of a sensor. In response to the triggering event, the controller automatically stops directing non-critical data to the first video buffer and directs critical patient data to the first video buffer. The detected disconnection of a sensor comprises a disconnected ECG electrode. The physiological parameter falling below a predefined threshold comprises a weakening pulse oximeter signal. The non-critical data comprises laboratory data, prescribed medication, patient educational data, advertising, historical patient health status, historical alarm data, video data, audio data, or email data. The non-critical data is transmitted to the display system, via the at least one network and said at least one port, from a remotely located database. The critical patient data comprises at least one of data a) indicative of a patient's health status requiring immediate attention from a health care provider, b) indicative of a patient's health status which should be brought to the attention of a health care provider but which is not time-critical, or c) designated by a health care provider as requiring substantially constant display. The physiological parameter measuring devices comprise ECG, blood pressure, $SpO_2$, cardiac output, temperature, capnography, BIS, $SvO_2$, or EEG measuring devices.

In another embodiment, the present specification discloses a display system for displaying critical patient data and non-critical data, comprising: a plurality of ports configured to connect said display system to a plurality of physiological parameter measuring devices; at least one port configured to connect said display system to at least one network; a display screen comprising a plurality of pixels divided into a first display region, having a first pixel count, and a second display region, having a second pixel count, wherein said first display region displays data from a first video buffer and wherein said second display region displays data from a second video buffer; and a controller for directing non-critical data to said first video buffer and for directing critical patient data to said second video buffer, wherein, in response to a triggering event, said controller decreases the first pixel count, thereby decreasing the first display region size, and increases said second pixel count, thereby increasing said second display region size.

Optionally, the triggering event is at least one of an alarm, a physiological parameter exceeding a predefined threshold, a passage of time, a physiological parameter falling below a predefined threshold, or a detected disconnection of a sensor. In response to the triggering event, the controller automatically stops directing non-critical data to the first video buffer and directs critical patient data to the first video buffer. The detected disconnection of a sensor comprises a disconnected ECG electrode. The physiological parameter falling below a predefined threshold comprises a weakening pulse oximeter signal. The non-critical data comprises laboratory data, prescribed medication, patient educational data, advertising, historical patient health status, historical alarm data, video data, audio data, or email data. The non-critical data is transmitted to the display system, via the at least one network and said at least one port, from a remotely located database. The critical patient data comprises at least one of data a) indicative of a patient's health status requiring immediate attention from a health care provider, b) indicative of a patient's health status which should be brought to the attention of a health care provider but which is not time-critical, or c) designated by a health care provider as requiring substantially constant display. The physiological parameter measuring devices comprise ECG, blood pressure, SpO$_2$, cardiac output, temperature, capnography, BIS, SvO$_2$, or EEG measuring devices. The critical patient data comprises a predefined set of values generated in real-time from said physiological parameter measuring devices.

In another embodiment, the present specification discloses a method for concurrently displaying non-critical data and a multitude of patient physiological parameters being monitored in real-time on a display screen, having a plurality of pixels divided into a first display region with a first pixel count and a second display region with a second pixel count, comprising: receiving monitored data from a plurality of patient physiological parameters; receiving stored data from at least one data network; buffering critical patient data in a first video buffer; buffering non-critical data in a second video buffer; displaying critical patient data in said first display region, wherein said first display region is in data communication with said first video buffer and not said second video buffer; displaying non-critical data in said second display region, wherein said second display region is in data communication with said second video buffer and not said first video buffer; and in response to a triggering event, decreasing the first pixel count, thereby decreasing the first display region size, and increasing said second pixel count, thereby increasing said second display region size.

Optionally, the triggering event is at least one of an alarm, a physiological parameter exceeding a predefined threshold, a passage of time, a physiological parameter falling below a predefined threshold, or a detected disconnection of a sensor. The non-critical data comprises laboratory data, prescribed medication, patient educational data, advertising, historical patient health status, historical alarm data, video data, audio data, or email data. The critical patient data comprises at least one of data a) indicative of a patient's health status requiring immediate attention from a health care provider, b) indicative of a patient's health status which should be brought to the attention of a health care provider but which is not time-critical, or c) designated by a health care provider as requiring substantially constant display.

The aforementioned and other embodiments of the present invention shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings.

DETAILED DESCRIPTION OF THE INVENTION

The present specification provides a dual display monitor which can be set up at a patient bedside to provide aggregated medical information related to the patient along with the patient's real time vital statistics. One of the two displays continuously shows the real time patient monitoring information whereas the other is used to display information such as when medicines were delivered, show lab results in reference to vital signs, and provide access to other remote hospital applications, typically only accessible via separate data terminals. The dual display monitor is connected to the hospital information system and has the capability of displaying local software applications and remote software applications via remote display software, such as, software made available by Citrix™. In addition, the dual display monitor can be connected to a central monitor configuration that can include up to four additional displays. These additional displays can be used to monitor more patients, display additional data, and/or host other applications.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
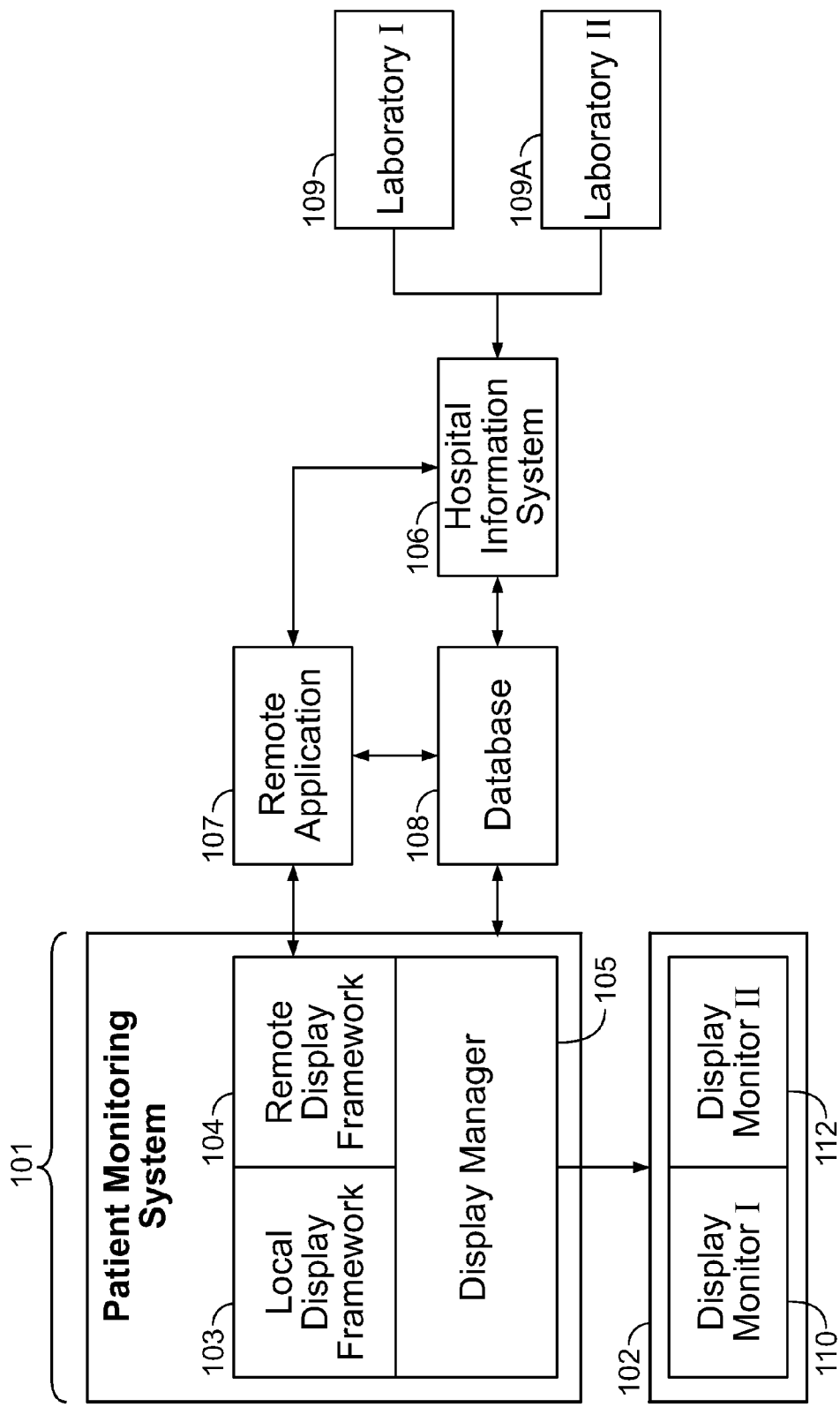
FIG. 1 is a block diagram illustrating an environment in which the dual display monitor is used, in accordance with an embodiment of the present invention.

FIG. 1 is a block diagram illustrating an environment in which the dual display monitor is used in accordance with one embodiment of the present invention. The dual display monitor 102, comprising a first display monitor 110 and a second display monitor 112, is installed by a patient's bedside and is connected to the patient monitoring system 101 through a display manager 105 included within said patient monitoring system 101. In various embodiments, the patient monitoring system 101 includes ports for a plurality of measuring devices, which includes but is not limited to, ports for blood pressure monitoring systems, heart rate monitoring systems, and pulse oximeter monitoring systems. The display manager 105 interfaces with a local display framework 103 and a remote display framework 104, both of which are also included within the patient monitoring system 101. The remote display framework 104 communicates with a remote application 107 which in turn collects information from a database 108 and a hospital information system (HIS) 106. The HIS 106 has access to data received from a plurality of laboratories 109, 109A. Data received from the laboratories 109, 109A comprises blood test reports, X-ray scan reports, among other data. The patient monitoring system 101 also interfaces directly with said database 108 and in turn, the HIS 106.

Patient monitoring information is fed to database 108 where the information is sorted and, in one embodiment, a subset of the information is fed to the hospital information system 106. First display monitor 110 displays real time patient vital statistics as obtained from the patient monitoring system 101. Real time patient statistics comprise, for example, numeric data (such as heart rate, systolic blood pressure, and cardiac output), alarm states (when a patient's current status violates a preconfigured alarm state) and other technical and medical status (such as anomalistic weakening of pulse oximeter signal or disconnection of ECG electrode(s)).

Database 108 comprises at least one storage memory that resides locally within the dual display monitor 102 as well as at least one storage memory external to the monitor 102 residing in proximity or remotely from the monitor 102. Thus, in one embodiment, some or all of the patient vital statistics data, communicated and displayed real-time by first display monitor 110, is also stored in local data storage residing within the dual display monitor 102. This locally stored patient data, in one embodiment, is used to create trend displays and to allow review of alarm data in clinical context. In one embodiment, at least a portion of the entire patient vital statistics data stored in local data storage residing within the dual display monitor is also available for posting to the hospital information system. Additionally or in alternate embodiments, some or all of the patient vital statistics data is communicated over a network for storage in a database that is external to the dual display monitor 102. The storage capacity of such an external database is typically large to accumulate data over a long period of time. Persons of ordinary skill in the art should appreciate that the external database may reside on a computer/server in proximity to the dual display monitor 102 and/or on a computer/server remote from the dual display monitor 102.

Data from the external database is exported to the hospital information system 106 using standard output formats such as HL7, Medibus. In one embodiment, data from the external database is pushed out to the hospital information system 106 at predetermined intervals. Additionally, the data is also accessible via queries to the external database, which in one embodiment, may be customized.

Second display monitor 112 displays information aggregated from the database 108 and the hospital information system 106. Information such as the patient's health trends, drug effects on the patient's vital statistics, lab results, among other data, are displayed on the second display monitor 112, provided by at least one or more underlying local or remote software programs. Hence, the information displayed on the second display monitor 112 enables caregivers to understand and analyze the patient's progress and response to drugs and hence, effectively respond to changes in the patient.

In one embodiment, local and remote software applications accessed on the dual display monitor 102 enable viewing of patient data stored in the external database in a way that enhances monitoring functionality at the patient bedside. For example, an ECG waveform review application, hosted on the monitor 102, allows waveform records over the last 72 hours to be reviewed, edited, forwarded and re-stored. In another example, a database application enables retrieval of readings from laboratories 109 and trends them for display. Persons of ordinary skill in the art should appreciate that such software applications may reside locally or be hosted on a separate bedside monitor, a central workstation or at a physician's office PC. In each case the patient data is retrieved from the external database and the editing session is run on the appropriately connected computer. Additionally, in further embodiments, the local and remote software applications accessed on the dual display monitor 102 also comprise applications other than those just related to providing patient monitoring functionality. For example, such software could be an entertainment; Internet or other network connectivity; or a patient education application or an email or video conferencing application or any other value-added application that would be advantageously evident to those of ordinary skill in the art. In one embodiment, fixed screen zones are established for patient applications. For example, patients are not allowed to cover up vital signs displays or they are restricted to using the second display monitor 112, in one embodiment, for email, video conference, or other patient activities.

In one embodiment, the dual display monitor 102 can be enabled in either patient mode or caregiver mode. In patient mode clinical settings cannot be changed but a controlled list of approved software applications, such as entertainment or patient education, can be run. The monitor is in patient mode unless a caregiver is in the room. Thus, for example, when the patient is in the room unattended the monitor would typically be in patient mode. The mode can be changed remotely by a caregiver. To change into caregiver mode the monitor is enabled to take a credential, password or RFID badge. In one embodiment, context sensitive disabling or minimization of patient mode is enabled. Thus, in the event of a change in clinical state [for example a certain alarm class (high priority)] the patient's application is disabled or minimized until cleared by a caregiver. Ideally, this would be configurable by the caregiver by alarm type or alarm class.

The dual display functionality of the monitor 102 of the present invention enables optimization between the display of real-time patient monitoring data and therefore related alarm contexts and the display of information from local or remote software applications accessed on the monitor 102.

Optimization is achieved by providing adequate screen real estate through a plurality of scenarios, such as, in the following various embodiments, wherein in a first embodiment, first display 110 is used for full time real-time monitoring while second display 112 is used for full time hosted application viewing. In another embodiment, first display 110 and second display 112 are both available for hosted application viewing but first display 110 is reserved for real-time monitoring when an "event of significance" occurs. In yet another embodiment, first display 110 and second display 112 are both available for monitoring during an "event of significance".

It should be appreciated that the presently disclosed system enables critical patient data, defined as data which a) is indicative of a patient health status requiring immediate attention from a health care provider or that is otherwise time-critical, b) is indicative of a patient health status which should be brought to the attention of a health care provider but which may not be time-critical, and/or c) is designated by a health care provider as requiring substantially constant display, to be displayed alongside non-critical data, defined as data which does not constitute critical patient data, without compromising the display of the critical patient data. It should further be appreciated that the functionality described herein is effectuated by a controller implementing a plurality of instructions, stored in memory local or remote from the display, and executed by at least one processor.

In another embodiment, there is only one display but a portion is pre-allocated as application display area. In another embodiment, there are two, three, four, or more separately controlled display regions in a single physical display. In another embodiment, there are two, three, four, or more separately controlled display regions in two or more physical displays. It should be appreciated that a display area or region can be a region of pixels located in one or more physical displays.

In yet another embodiment, there is only one display and applications can take all of the screen area but surrender control during an "event of significance". In this case, it is possible that a caregiver is running a software application and hiding/covering some or all of the monitor's real-time vital information when a patient's status changes. In such cases, in one embodiment, the monitor is enabled to minimize all applications for certain types of patient events. Thus, certain events (alarms of a certain type or priority) automatically minimize all applications thus displaying the monitoring message. In another embodiment, the application is left running but a message (which must be responded to) is posted on top of any and all applications. If the message is not responded to, then the application is automatically minimized. Still alternatively, all applications could be minimized automatically after a configurable time out. Thus, in the event an application user leaves the application running (covering some or all of the real-time vitals monitoring functionality), the application is minimized after a period of no-activity. In various embodiments, the period of inactivity is set to 1, 3, 5, 15, or any other user determined value. For example, assuming a 3 minute inactivity threshold, if a user accesses an application and enters data for 5 minutes, the application will not minimize because of the activity. When the user is called away from the monitor, after 3 minutes the application will be minimized automatically.

Persons of ordinary skill in the art should appreciate that an "event of significance" could be a plurality of predefined states/scenarios/thresholds/rules. In one embodiment, an "event of significance" is user defined (such as, for example, Heart rate>140 bpm, Systolic blood pressure>150 or <90). In another embodiment, an "event of significance" is defined by an arbitrarily complex set of rules to define when non-critical applications should surrender to the real-time monitor. In yet another embodiment, the "event of significance" is based on alarm status (such as: any alarm, any high priority alarm, and any medium or higher priority alarm). In still yet another embodiment, the "event of significance" is capable of being overruled by a user. Thus, a user may override and run an application by deciding that an alarm is actually not real.

In one embodiment, "events of significance" related functions are managed by a software module, hereinafter referred to as the 'clinical context manager'. The clinical context manager monitors the patient state and continuously compares it to the rules that have been established (defaults or user defined). Accordingly, the context manager signals hosted software applications to be displayed or minimized.

Further, based on the patient's state, the context manager can trigger additional activities, which may be default behaviors or they may be configured by the user. They may be configured based on alarm type or severity, or they may be based on clinical indexes that are currently being monitored. The additional activities that are triggered may be of several different types, such as, but not limited to, the following:
  a) logging additional data into the local or external database
  b) launching an application that retrieves additional information from a local or external database and presents the current state in a clinical context in the application area.
    1. For example, where a patient's blood pressure is dropping gradually, the patient's change in state is noted by the clinical context manager and an application is launched that retrieves the complete blood pressure history and plots the recent change in context to the historical record. This data is displayed in the application window.
    2. Where a patient is a diabetic, a user may select a default clinical context of diabetes for this patient (or it may be selected automatically if the diabetes diagnosis was retrieved from a health record). These activities are user configurable. Part of the "diabetes" clinical context default rules may be to retrieve most recent blood sugar reading in the event of successive low pressure readings. In this case, multiple low readings would trigger an application to retrieve the extended blood pressure history and the extended laboratory and blood draw data and present this data in an application window. A clinician who then checked on the patient would see the current monitoring status and the relevant data presented in a clinically appropriate manner.
    3. In another example, the primary display is displaying ECG, SpO2 and NIBP values for a patient. Initially, the patient is in normal sinus rhythm but over time begins to develop an increasing number of abnormally conducted beats. The clinical context manager launches a trending application (either locally on the monitor or on a remote workstation) that renders a trend graph of the number of abnormal beats versus time for the last few hours. This trend will draw the attention of the caregiver to a parameter that the clinical context manager has determined is changing.
    4. In yet another example, the clinical context manager will launch a trending application if a patient's mean heart rate increases by more than 15%. In this example, the trending application will display the patient's heart rate for the last 6 hours and render the data at 30 second resolution with updates in real time.

Figure 2:
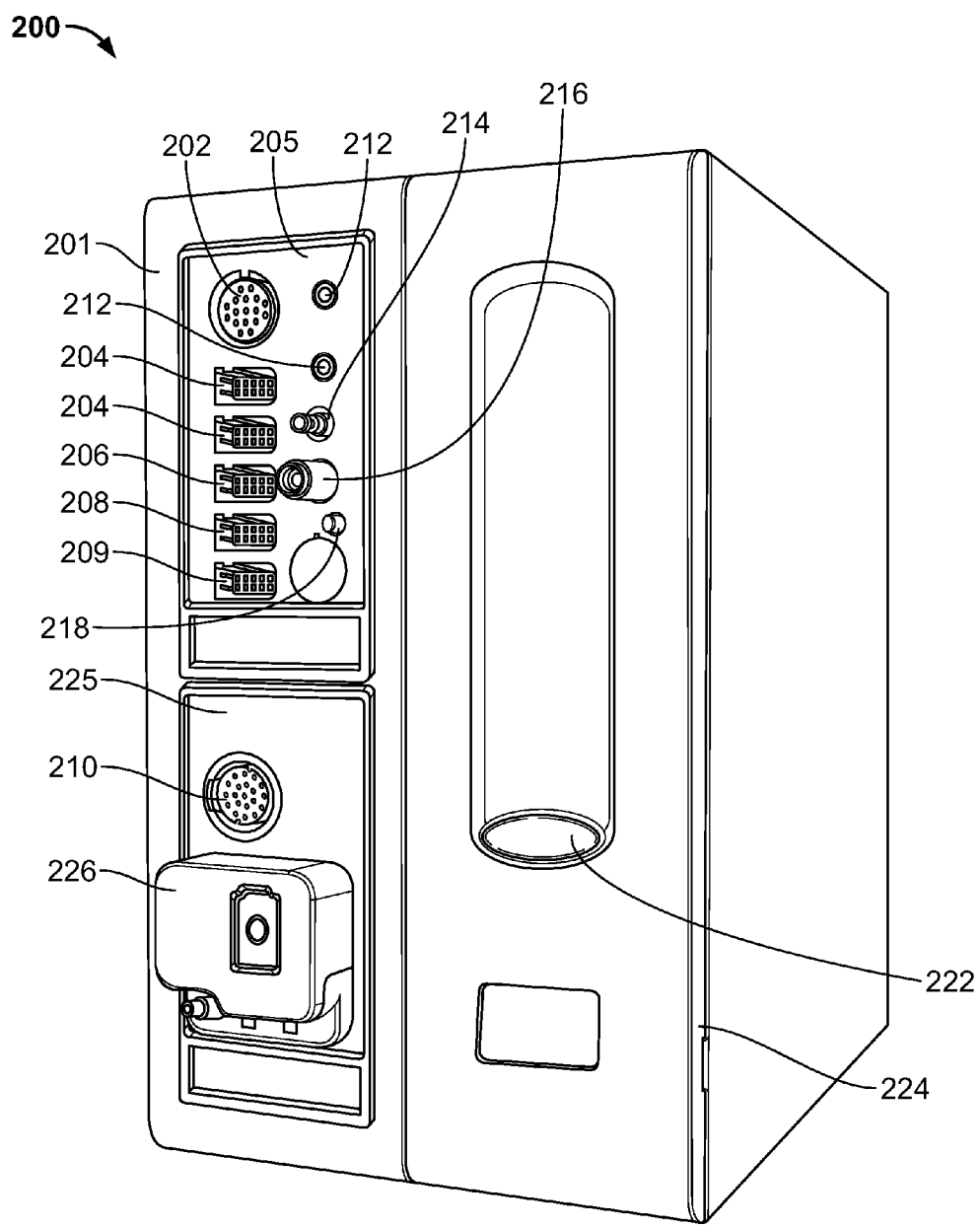
FIG. 2 illustrates a patient monitoring system, as shown in FIG. 1, that is employed, in one embodiment, to support and/or control dual display functionality.

FIG. 2 illustrates a patient monitoring system, as shown in FIG. 1, that is employed, in one embodiment, to support and/or control dual display functionality; The patient monitoring system 200 supports the connection of two display units such as video display units (VDU), liquid crystal display (LCD) screen, among any other display type known in the art. The patient monitoring system 200, which in one embodiment comprises first module 205 and second module 225, is provided with a plurality of ports on a panel 201 for enabling connection with display units, a hospital database, and other networks.

First module 205 comprises a plurality of ports that provide interfaces to patient connected cables, transducers or sensors. In one embodiment, port 202 is the connector for an ECG cable. This cable is connected to the electrodes on the patient and ECG analysis is performed by the patient monitor.

In one embodiment, port 204 is a connector for an Invasive Pressure cable. This cable is connected to a catheter placed inside the patient.

In one embodiment, port 206 is a connector for connecting an appropriate $SpO_2$ cable. The cable is connected to a $SpO_2$ sensor and attached to the patient. The pulse oximeter function is inside the patient monitor.

In one embodiment, port 208 is a connector for a cardiac output cable, which would attach to a catheter put into the patient. The cardiac output analysis is performed by the patient monitor.

In one embodiment, port 209 is a connector for a dual temperature cable. The temperature analysis is performed by the patient monitor.

In one embodiment, port 212 is a high level output designed to provide an external analog interface to an ECG or Invasive pressure waveform.

In one embodiment, port 214 is a connector to an adult NIBP adapter hose.

In one embodiment, port 216 is a connector to a neonatal NIBP adapter hose.

In one embodiment, button 218 is provided to enable a "Stop" NIBP control.

In one embodiment, ports 210 and 226 of second module 225 are related to a capnography gas analyzer. Port 210 is a connector which attaches to the patient for mainstream capnography. Port 226 is a connector for side stream capnography. The second module 225 could be used for any of a number of different specialty monitoring applications such as BIS (bispectral index), SVo2 or EEG, as manufactured by Spacelabs Healthcare LLC.

Persons of ordinary skill in the art should appreciate that the patient monitoring system 200 of the present invention allows appropriate interfaces for connectivity to additional and/or alternate medical/patient monitoring devices that are manufactured by third party vendors. For this purpose, a plurality of connections or ports may be provided a panel of the patient monitoring system 200, hereinafter referred to as flexports or data interfaces, to third party devices or networks. For example, there could be a case where a particular respirator or a pulse oximeter made by a third party vendor/manufacturer needs to be used. For devices which use the flexport interface, the data is then displayed on the patient monitoring system 200 (such as in the form of waveforms, numeric data, indices and/or alarms) and can be trended and reviewed along with the other data. Data from these flexport devices can also be exported to an external database (as described with reference to database 108 of FIG. 1). Similarly, connections to a network and connections to the two video outputs for the display monitors can be found on the back panel.

Figure 3:
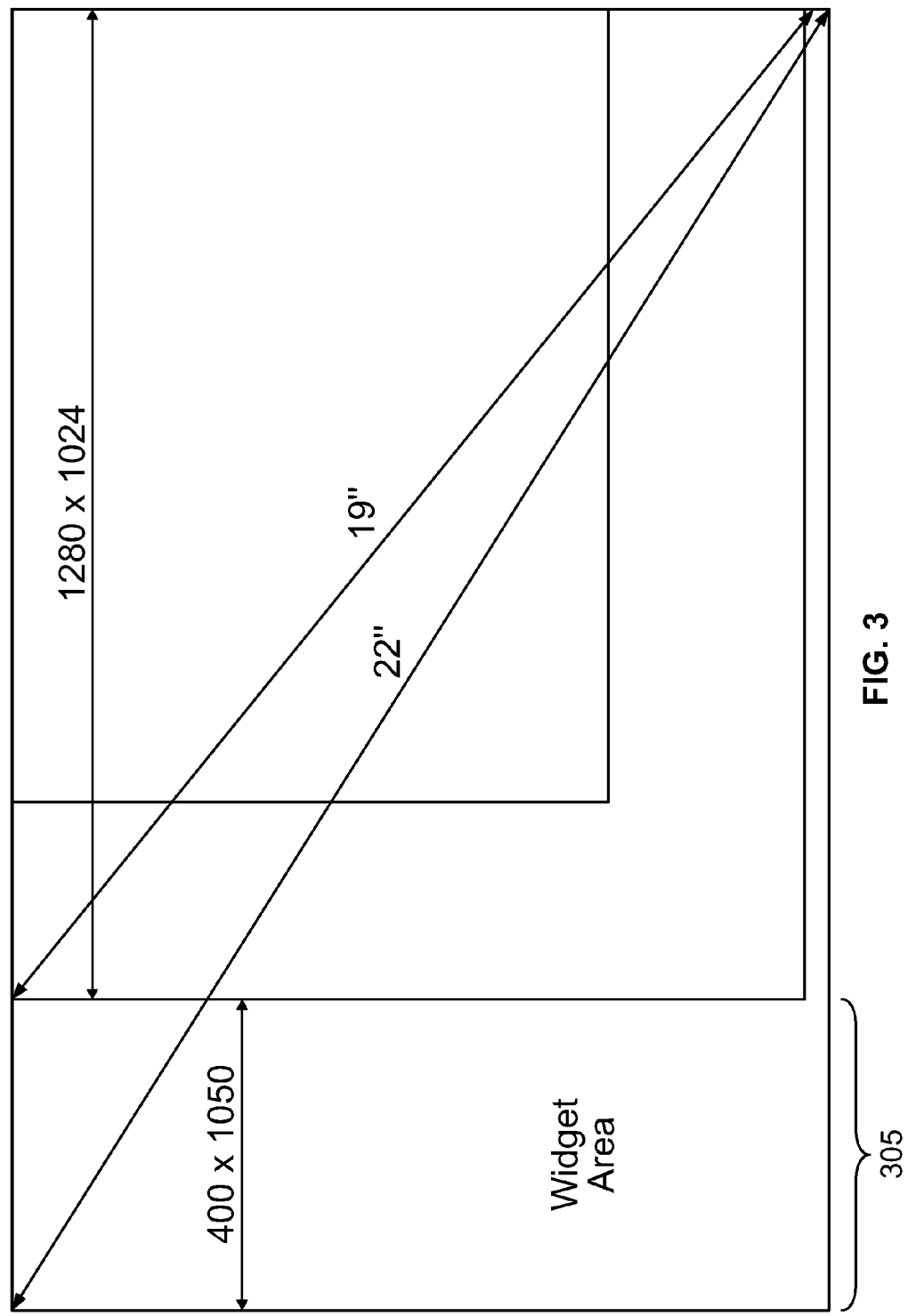
FIG. 3 is a block diagram illustrating screen size and usage differences of the dual display monitor among multiple embodiments of the present invention.

In one embodiment, and as mentioned with respect to FIG. 1, the dual display monitor 200 supports a first display unit and a second display unit, which in one embodiment are 19 inches with a 4×3 ratio, and wherein the resolution of real-time patient monitoring display is 1024×768 and that of software application display is 1280×1024 pixels. In another embodiment, the two display units measure 22 inches diagonally and have a 16×9 (wide aspect) ratio. FIG. 3 is a block diagram illustrating screen size and usage differences of the dual display monitor among multiple embodiments of the present invention. In one embodiment, in which both display units measure 22 inches, both display units have a resolution of 1280×1024 pixels. In one embodiment, in which both display units measure 22 inches, the vertical screen height of both monitors is approximately the same as that of the 19 inch display units, and the extra horizontal screen space 305 is reserved for widgets. In one embodiment, the vertical screen height of the 22 inch display units differs from that of the 19 inch display units by +/−0.2 inches. In an embodiment, a single mouse control and a single keyboard control is provided as input devices for both the displays. Input may also be provided via 'touch screen' functionality provided to the two displays.

In an embodiment, the application display presents remote or virtual applications. In various embodiments, there are a number of controls that allow caregivers to decide how they want to see the information. In an embodiment, caregivers may preset the application display screen. For example, if all cardiologists want to see the same data, the application display screen may be preset to a standard cardiology data display. A caregiver may choose an option entitled 'cardiology' and obtain all cardiology related information available with the hospital information system with or with-out any specific patient context. In an embodiment options presented on the monitor screen may be selected by using voice recognition technology based on radio frequency identification (RFID).

In various embodiments the application display screen is a multi-purpose device/monitor that may be used as a high definition television (HDTV), as a user interface for sending emails, as an interface for patient education, as a user interface for running bedside applications (patient entered data such as pain score), as a screen for playing video games, for conducting mental acuity tests, among other optional activities. In an embodiment, the application display can be a tablet PC that is provided to a clinician that connects to patient bedside monitor. Thus, the second display may not be on the monitor 200, but may be provided remotely to the caregiver.

Referring again to FIG. 2, a power switch 222 is provided on a panel for turning the dual display monitor 200 on or off. In one embodiment, the power switch 222 is secured to the power supply board by elastomer prongs and is positioned between the power supply board and a panel bezel. The power switch 222 is back lit for enabling easy viewing of the monitor's power status. An extra universal serial bus (USB) port 224 is provided on a side of the front panel 201 for connecting any ancillary monitoring device or a supported USB accessory.

Figure 4:
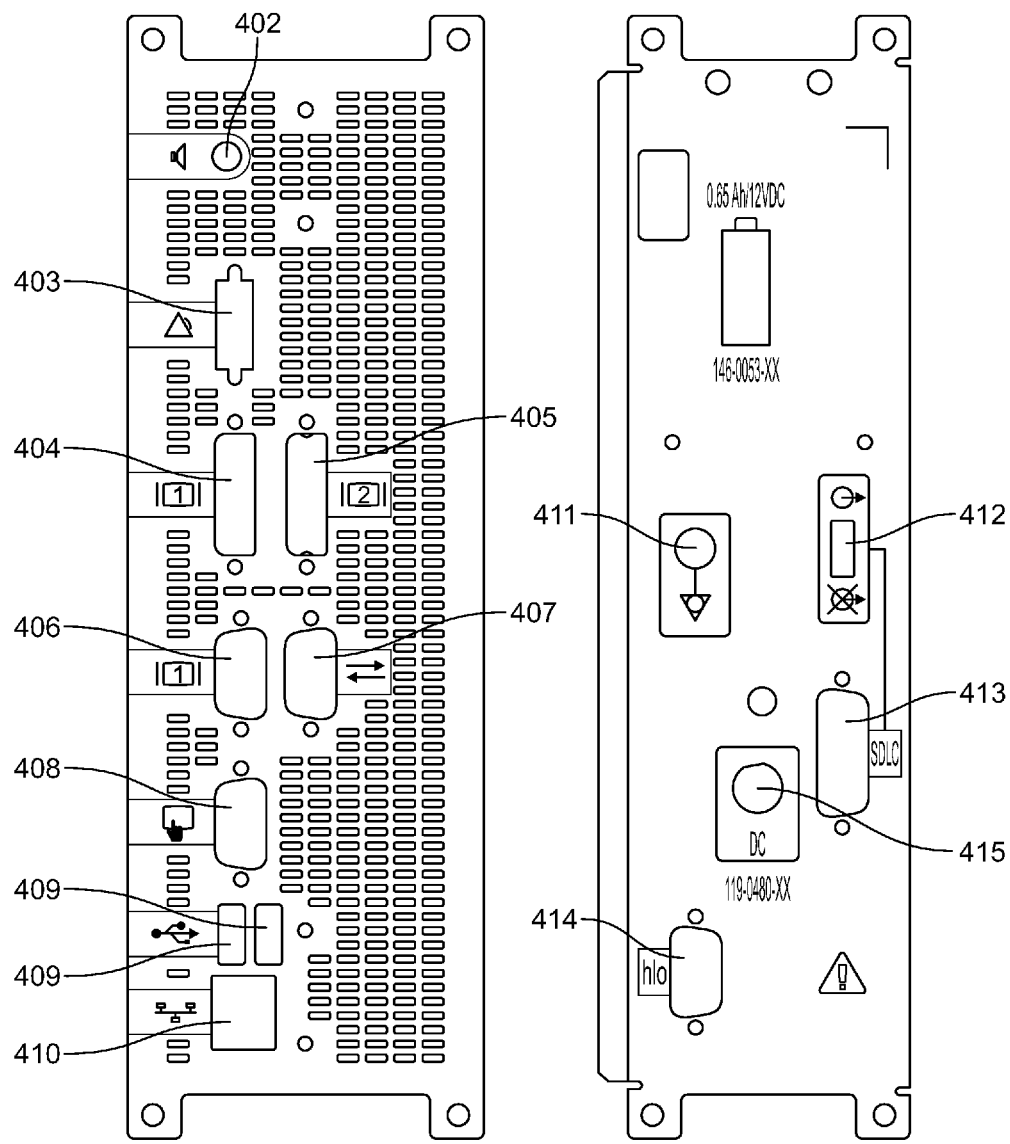
FIG. 4 illustrates the rear panel of a patient monitoring system that is employed, in one embodiment, to support and/or control dual display functionality.

FIG. 4 illustrates the rear panel of a patient monitoring system that is employed, in one embodiment, to support and/or control dual display functionality. As discussed above, a panel of the patient monitoring system may contain a plurality of flexports or data interfaces for connectivity to additional and/or alternate third party patient monitoring devices. In one embodiment, a panel includes an audio output port 402 and an alarm relay output port 403. The panel also includes a first DVI video output port 404 and a second DVI video output port 405 for a second independent display. A VGA video output port 406 is also included for connecting a display. The panel additionally includes serial port 407 and another serial port 408 for an external touchscreen. Two USB-A ports 409 and an Ethernet port 410 are also included. The panel includes an equipotential terminal 411, SDLC terminator switch 412, SDLC/Power output 413, and high level analog output 414. In addition, the panel contains a DC power input port 415 for connection of a power cable to the patient monitoring system.

Figure 5:
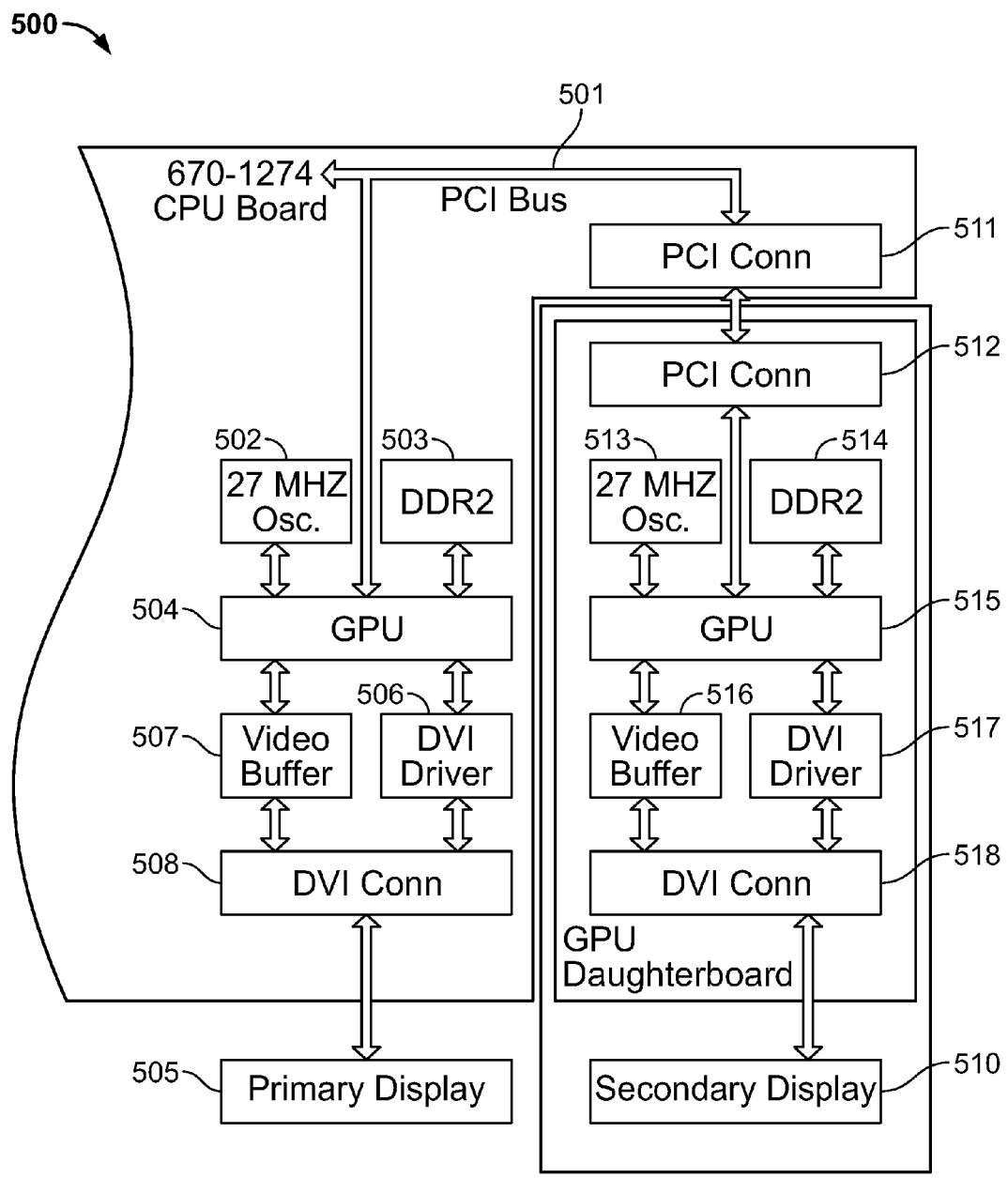
FIG. 5 illustrates a block diagram of the video configuration of the dual display monitor, in accordance with an embodiment of the present invention.

FIG. 5 illustrates a block diagram of the video configuration of the dual display monitor 500, in accordance with an embodiment of the present invention. A PCI data bus 501 carries data transmitted from a processor to one of two displays, a primary display 505 and a secondary display 510. With respect to the primary display 505, the PCI data bus 501 interfaces with a processing unit 504 which is in data communication with oscillator 502 and memory 503. The processing unit 504 processes data for display and transmits it to a video buffer 507 and display driver 506. Display data is then interfaced to the primary display 505 via an interface 508.

Similarly, with respect to the secondary display 510, the PCI data bus 501 interfaces with a PCI interface unit 511, which interfaces with PCI interface unit 512 and communicates with processing unit 515, which is in data communication with an oscillator 513 and memory 514. The processing unit 515 processes data for display and transmits it to a video buffer 516 and display driver 517. Display data is then interfaced to the primary display 510 via an interface 518.

The architecture of the Dual Display system enables improved data access and an integrated display of data from multiple sources. In various embodiments the graphical user interface (GUI) of the display comprises a plurality of widgets with which a user (a caregiver or a patient) may interact. In one embodiment, the widgets are displayed as borderless windows or icons. In one embodiment, the widgets are set to a predefined location. In one embodiment, the widgets are non-resizable. Examples of the widgets comprise widgets for displaying patient health trends, lab data, event triggers, alarm history, clinical data, treatment protocols, launching clinical applications, launching hospital applications, or printing data.

In an embodiment, Windows Dynamic Network Access (WinDNA) provides access to custom applications running at fixed screen locations via the dynamic network access (DNA). Thus, in one embodiment, DNA is a software application that allows third party applications (such as, but not limited to HIS) running on another computer to host a session on the bedside monitor. The data to drive the display and to interact with the user at the display is exchanged via a network configuration.

Thus, WinDNA allows users to view and control Windows applications on the display. Input to the WinDNA can be done using a mouse, a keyboard, and via touch-screen. In one embodiment, a thin-client, embedded in the DNA-enabled display, allows the users to launch applications installed on the server using the hospital's existing network infrastructure.

Figure 6:
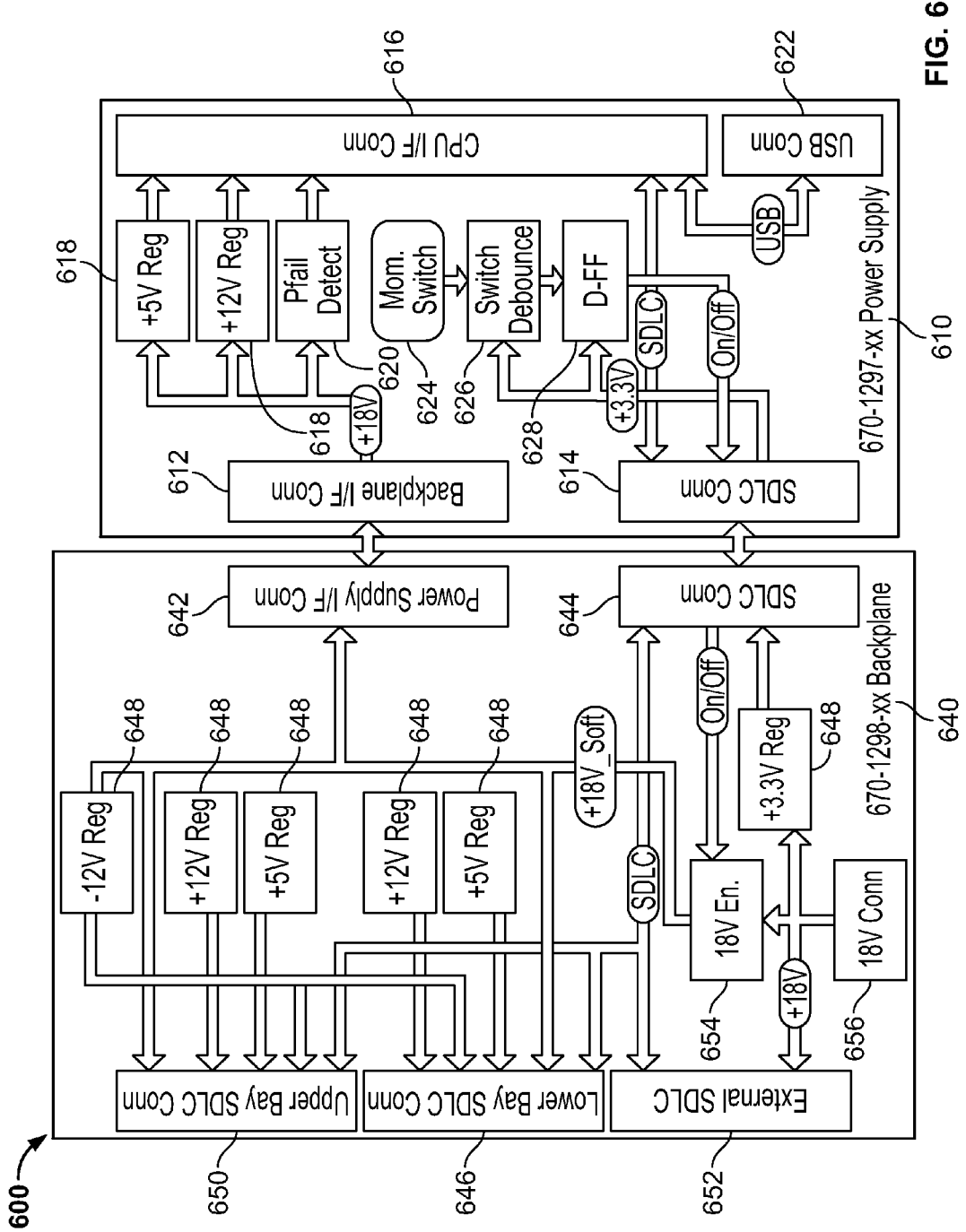
FIG. 6 illustrates a block diagram of the power configuration of the patient monitoring system that is employed, in one embodiment, to support and/or control dual display functionality.

FIG. 6 illustrates a block diagram of the power configuration 600 of a patient monitoring system that is employed, in one embodiment, to support and/or control dual display functionality. In one embodiment, the power configuration 600 includes a power supply component 610 and a backplane component 640. The power supply component 610 and backplane component 640 interface via two separate connections. The first connection is an interface between a Power Supply I/F Connector 642 on the backplane component 640 and a Backplane I/F Connector 612 on the power supply component 610. The second connection is an interface between an SDLC Connector 644 on the backplane component 640 and an SDLC Connector 614 on the power supply component 610.

Referring now to the power supply component 610, the Backplane I/F Connector 612 interfaces with a CPU I/F Connector 616 through two power regulators 618 and a Power Fail Detect circuit 620. Additionally, the CPU I/F Connector 616 has a USB interface with a USB Connector 622 on the power supply component 610. Further, the power supply component 610 includes a Momentary Switch 624 which interfaces with a Switch Debouncer Circuit 626, which, in turn interfaces with a Data or Delay Flip-Flop (D-FF) Circuit 628. The D-FF 628 interfaces with the SDLC Connector 614 on the power supply component 610.

Referring now to the backplane component 640, the Power Supply I/F Connector 642 interfaces with a Lower Bay SDLC Connector 646 and an Upper Bay SDLC Connector 650 both directly and through a power regulator 648. Both the Lower Bay SDLC Connector 646 and Upper Bay SDLC Connector 650 interface with additional power regulators 648. The Power Supply I/F Connector 642 also interfaces with an External SDLC Connector 652 through an 18V En. 654 and 18V Connector 656. The SDLC Connector 644 on the backplane component interfaces directly with the Lower Bay SDLC Connector 646, Upper Bay SDLC Connector 650, and External SDLC Connector 652. Further, the SDLC Connector 644 also interfaces with the External SDLC Connector through a power regulator 648.

Figure 7:
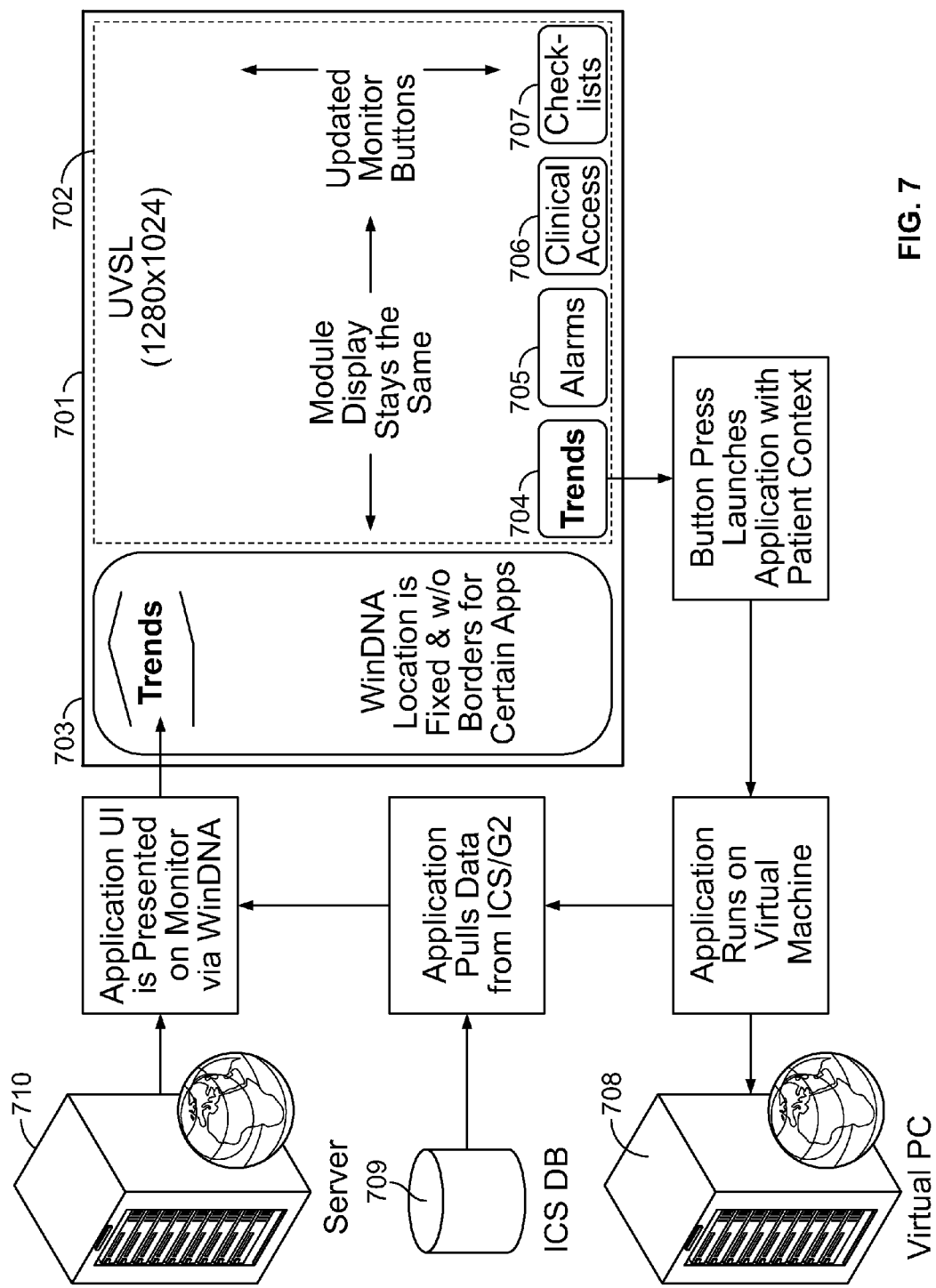
FIG. 7 illustrates a block diagram of the data access and display architecture of one embodiment of the present invention.

Referring to FIG. 7, a display 701 comprises a data display region 702, a plurality of data access buttons 704, 705, 706, 707, and a fixed region 703 that displays data accessed when the data access buttons 704, 705, 706, 707 are activated. For example, when a trend button 704 is pressed or actuated, a command is transmitted to a virtual PC 708 which causes an application corresponding to conducting trend analyses to execute and access, retrieve, or otherwise obtain data from a database 709. The accessed data is then communicated to a second server 710, which formats the accessed data for display in region 703. In one embodiment, the display of region 703 is controlled entirely by the second server 710. It should be appreciated that each of the buttons 704, 705, 706, 707 correspond to executing an application, which is stored in the memory of the virtual computer 708 and executed by a processor in the virtual computer 708. In one embodiment, the data access button 704, 705, 706, or 707 for whichever application is running is highlighted to inform the user which application is being displayed. It should further be appreciated that the buttons can be configured to cause applications on the Virtual PC to access data relevant to patient health trends, lab data, event triggers, alarm history, clinical data, or protocols, to launch checklists, to launch clinical applications, to launch hospital applications, or to print data.

In one embodiment, the buttons are caused to be displayed by a monitor that, upon boot up, accesses an XML configuration file which defines button location, size, graphic, text, what executable application on a remote PC is related to the displayed button, context parameters to pass, behavior of WinDNA at launch, such as fixed, float, border size, among other parameters.

Figure 8:
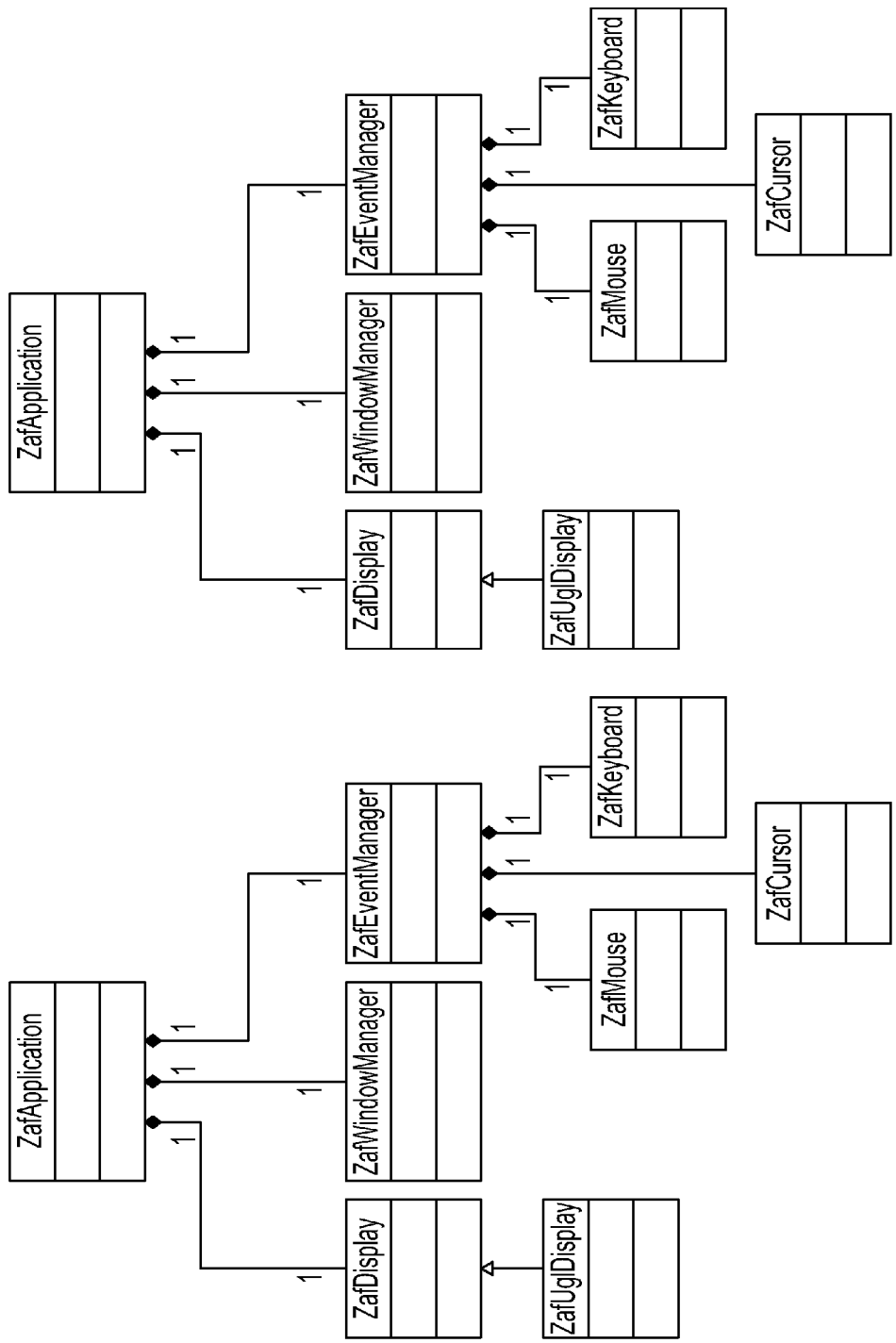
FIG. 8 illustrates an architectural block diagram of the dual display monitors, in accordance with an embodiment of the present invention.
Figure 9:
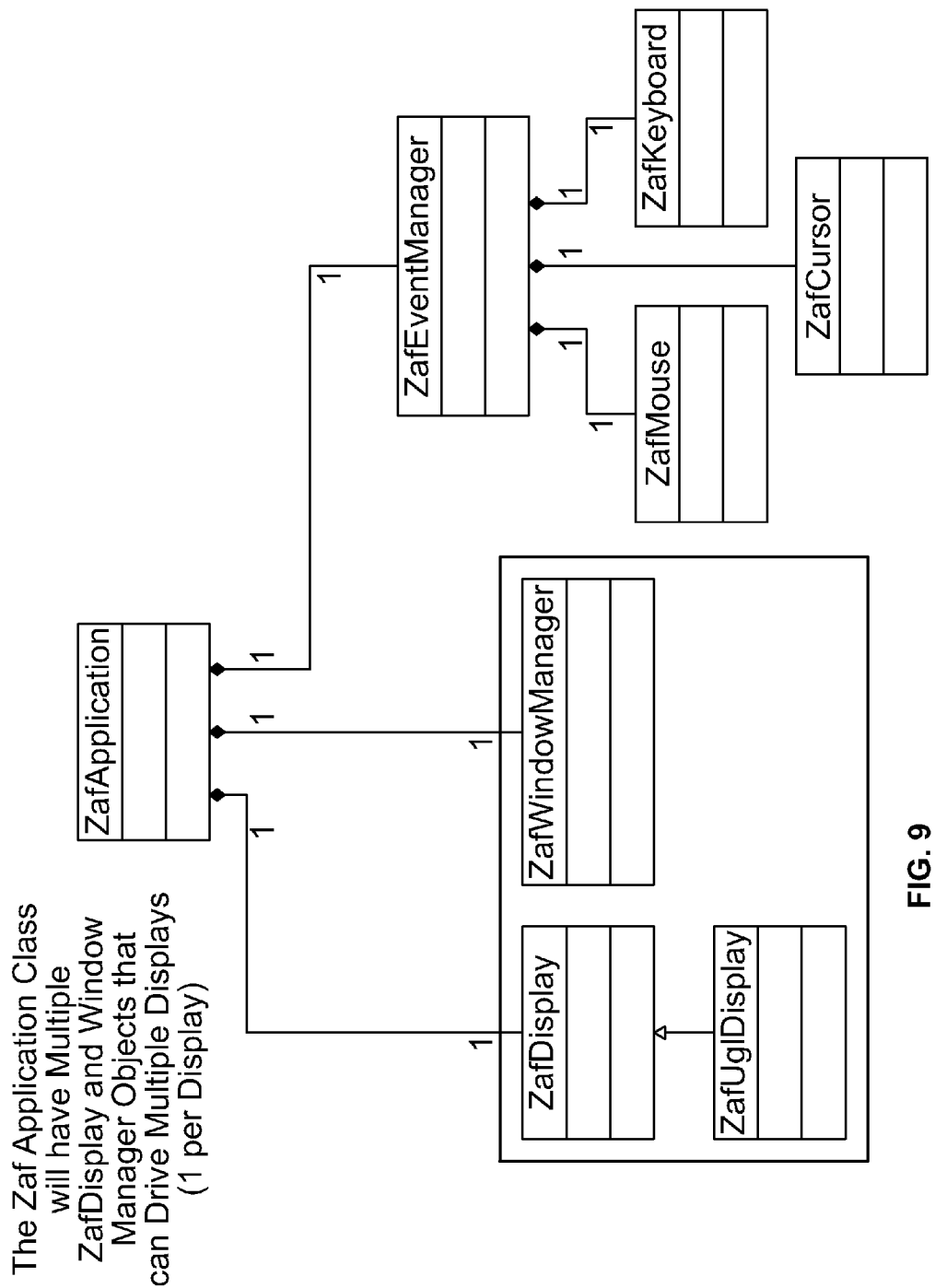
FIG. 9 illustrates an architectural block diagram of the dual display monitors, in accordance with another embodiment of the present invention.

Referring to FIGS. 8 and 9, which are architectural block diagrams of the dual display monitors, a top layer application class is driven by display, window manager, and event manager objects. The event manager object is further dependent upon various inputs, such as a mouse, cursor, and keyboard.

Figure 10:
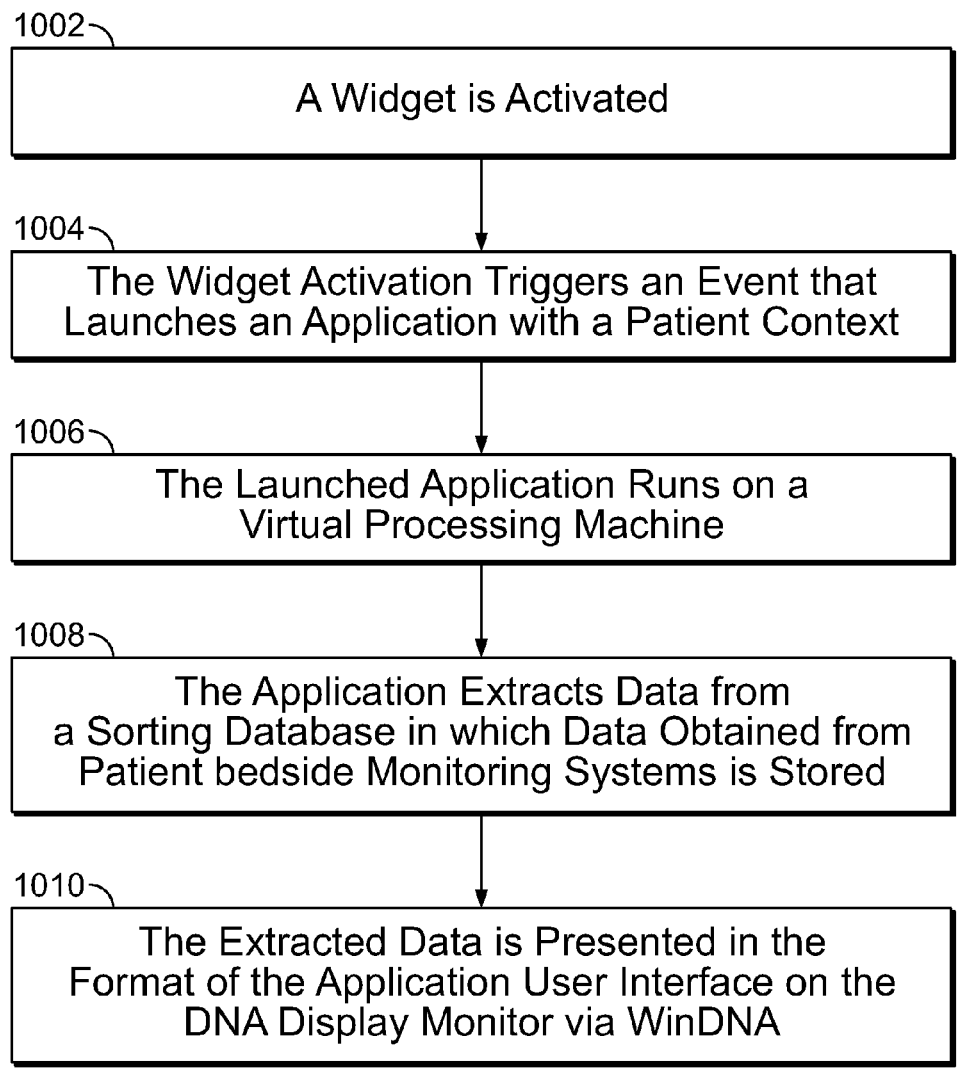
FIG. 10 is a flowchart illustrating the events that take place upon activation of a widget on a display monitor, in accordance with an embodiment of the present invention.

FIG. 10 is a flowchart illustrating the events that take place upon activation of a widget on a display monitor. A widget, such as a trend, alarm, or other data access button, is activated

1002. In an embodiment, widget activation triggers 1004 an event that launches an application with respect to a specific patient. The launched application 1006 runs on a virtual processing machine (computer). The application extracts 1008 data from a sorting database in which data obtained from patient bedside monitoring systems is stored. The extracted data 1010 is presented in the format of the application user interface on the display monitor via WinDNA.

Exemplary Use I

In one exemplary use, a 42 year old male motor cycle accident victim is mechanically ventilated in the Surgical Intensive Care Unit (SICU) of a large urban hospital. He suffered a ruptured spleen which was removed; fractured left leg, left arm, left ribs T6-9; and currently is in respiratory and renal failure. During the first 48 hours of admission he required high oxygen concentrations for severe hypoxemia which precipitated acute respiratory distress syndrome (ARDS). The critical trauma patient is diagnosed with multiple organ system failure and ARDS and is placed on permissive hypoxia protocol to prevent further damage from oxygen toxicity due to high fraction of inspired oxygen ($FiO_2$) settings on a ventilator.

The physician has written an order for oxygen weaning protocol (permissive hypoxia); the patient is on a cardiac monitor with clinical agent application and mechanical ventilation with supplemental oxygen. Minimal $FiO_2$ settings are maintained ($O_2$ concentration less than 40%) on the ventilator for improved patient outcome (less lung injury from prolong high level oxygen therapy) and fewer SICU days. The oxygen weaning protocol ordered by the physician is displayed on the dual display monitor when the protocol widget is actuated. The protocol may be displayed in the second or fixed region of the monitor as "keep $SpO_2$ less than 92% but greater than 88% by decreasing ventilator $O_2$ concentration by 2% no more than once per hour."

In an embodiment, this protocol is displayed in the basic clinical agent format and may (or may not) flash alerts when $SpO_2$ protocol levels are reached to hasten nurse/respiratory therapist work flow and more efficiently generate patient treatment which in turn may decrease number of SICU days. Without the protocol display, the nurse/therapist will have to locate protocols by time consuming searches through multiple files and, patient treatment and work flow would be less efficient.

Exemplary Use II

In another embodiment, a 78 year old female patient is awaiting ablation evaluation in Critical Care Unit (CCU), and persists with frequent episodes of Atrial fibrillation (AFib) lasting in excess of an hour. The patient is in CCU for evaluation of LA ablation to treat chronic persistent atrial fibrillation. She is on a cardiac monitor with ECG algorithm, oxygen at 2 L/min nasal cannula and has a history of dizziness, shortness of breath and fatigue.

The physician has written an order for AFib Burden Protocol while awaiting results for ablation evaluation. The patient has been classified as Class II-A for AFib and takes aspirin 81 mg, digoxin 0.14 mg and atenolol 50 mg daily. She has a peripheral IV maintenance line for access. The patient was safely treated pharmacologically for reversible episodes of A Fib. Her physician has placed her on his protocol of treatment for her specific classification and evidence of complications. The following protocol displays on the dual display monitor whenever the ECG algorithm detects A Fib and begins to track the amount of time A Fib is consistently present: "after 30 minutes of consistent A Fib, give 150 mg of amiodarone slow IVP (over 10 minutes) if PFTs with DLCO are on file, if no PFTS with DLCO, then give 20 mg/min procainamide until 17 mg/kg dose is reached or until resolution of A Fib or until bradycardia (whichever occurs first)." The dual display monitor would also flash when the ECG rhythm returns to normal. Without the protocol display, the nurse will have to locate protocols by time consuming searches through multiple files and patient treatment and work flow would be less efficient.

Exemplary Use III In another embodiment, a 66 year old male was receiving treatment for alcoholic pancreatitis in the ICU of an urban hospital and experienced a heart attack. The patient is on a cardiac monitor with IV access. As the patient went into Ventricular fibrillation (V Fib) and the cardiac monitor began to sound an alarm, the attending nurse selected the Cardiopulmonary resuscitation (CPR) protocol button on the dual display monitor. The dual display monitor displayed the following: (1) the current Advanced Cardiac Life Support (ACLS) reference flowchart for decision making, (2) CPR medications calculated for this patient's current weight and (3) a reference diagram with index of their hospital's crash cart to aid in the location of medications and supplies. From the onset of CPR the on screen ACLS reference card was used for decision making and saved valuable time since the physician did not need to locate his card. The medication list was also time efficient as it was clearly displayed and patient specific.

As CPR progressed, the patient became more difficult to bag and mask ventilate, and the physician was unable to intubate. The decision was made to use an LAM device to ventilate the patient but the respiratory therapist could not locate one on the crash cart. Using the dual display monitor and index of the crash cart, the respiratory therapist was able to identify the location of the LAM device so it could be used to ventilate the patient until an anesthesiologist could arrive to intubate. After 27 minutes of effective and efficient CPR the patient was stabilized and placed on a ventilator.

Using the physician's pocket ACLS card to direct care is the standard of care, but slows the process when the card is misplaced or difficult to read from age. Displaying ACLS protocol adjacent to the cardiac monitor on the DNA monitor is more time efficient during a critical procedure, allows for online medication calculations and improves readability. Searching a crash cart for supplies is a slow process and in the heat of the moment infrequently used items can be over looked. Without the on screen display and index of the crash cart, the LAM device would not have been found and effective ventilation could not have been performed which may have altered the patient outcome.

Exemplary Use IV

In another embodiment, a cardiologist has a complex chronic heart failure patient in CCU with multiple intravascular lines in place on multiple medications to manage preload and after load. The cardiologist seeks to visualize and assess the effect of treatment options on hemodynamic indices. The patient is on a cardiac monitor with a DNA display, PA line and/or other device interfaces (such as USCOM) for continuous or episodic hemodynamic measures.

Figure 11:
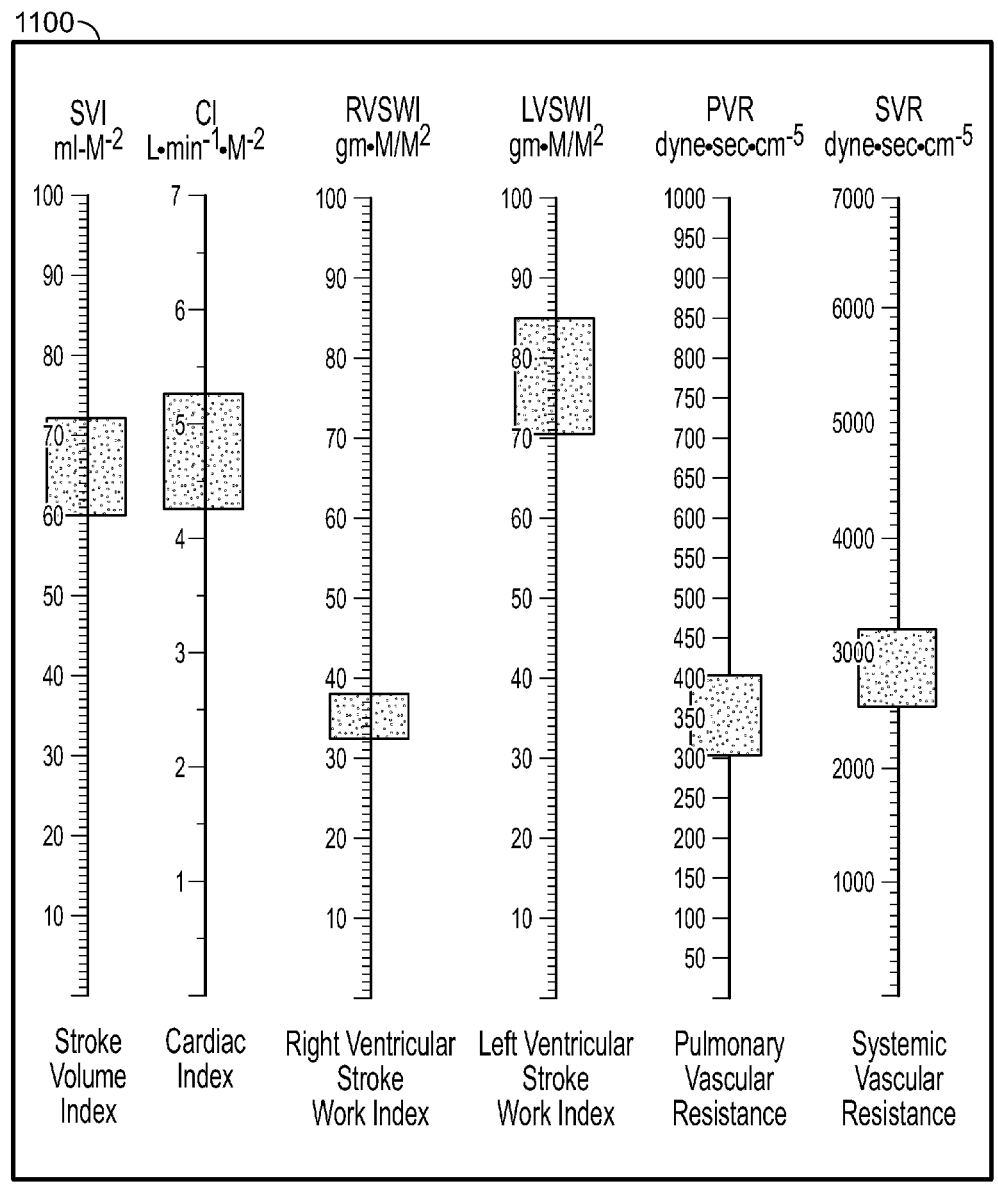
FIG. 11 illustrates a plot of hemodynamic indices displayed on a display monitor, in accordance with an embodiment of the present invention.

A 68 year old male patient with seven year chronic congestive heart failure history presents with both right and left side heart failure. Measures are available for SVI, CI, RVSWI, LVSWI, PVR, and SVR over a 24 hour period for a three day course of medication administration. The physician wants to plot the hemodynamic indices. Using the grid illustrated in FIG. 11, the dual display monitor interfaces with the data collection devices of the cardiac monitor and plots the hemodynamic values 1100. Without the data grid display, the physician will have to locate data by time consuming searches through multiple files and patient treatment and work flow would be less efficient.

Hence the dual display monitors may be used by clinicians or caregivers for accessing physiological waveforms and measurements as well as real time patient related information at the point of care (i.e., patient bedside) in order to provide speedy and accurate diagnosis and treatment.

Exemplary Use V

A 62 year old man is admitted to the emergency room due to a fainting episode at home. He is monitored while a number of different tests are run. While he is being monitored the clinical context manager is alerted that he has had two episodes of cardiac pause events that lasted 2.6 and 3.1 seconds; each of these events is posted to the external database. The monitor is configured to launch an application that reviews this data and retrieves the recommended clinical protocol which is to seek a cardiology consultation and to consider an implantable defibrillator. When the clinician returns to check on the patient she discovers the application displaying the recent event along with the suggested next steps.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A patient monitoring system, comprising:
   a display screen connected to a plurality of physiological parameter measuring devices, said display screen comprising a first region for displaying real time physiological parameter data and a second region separate from said first region;
   a database comprising a memory for storing patient data; and
   a controller programmed to generate a response to a critical event, said event comprising a physiological parameter exceeding or falling below a predetermined range of values, wherein said response comprises retrieving a recommended treatment protocol for the patient from said database to address the critical event and displaying said protocol on the second region of the display.

2. The system of claim 1, wherein the physiological parameter measuring devices comprise ECG, blood pressure, $SpO_2$, cardiac output, temperature, capnography, BIS, $SvO_2$ or EEG measuring devices.

3. The system of claim 1, wherein the database is remotely located.

4. The system of claim 1, wherein the patient data stored in the database includes patient health trends, lab data, event triggers, alarm history, clinical data, and treatment protocols.

5. The system of claim 1, wherein the display screen further comprises a plurality of data access buttons that can be actuated by a user to retrieve patient data.

6. The system of claim 1, wherein in an absence of a critical event, the second region of display screen is configured to launch applications for patient use.

7. A method for monitoring a patient, comprising:
   connecting a display screen to a plurality of physiological parameter measuring devices, said display screen comprising a first region for displaying real time physiological parameter data and a second region separate from said first region;
   storing patient data in a database comprising a memory;
   recognizing a critical event, said event comprising a physiological parameter exceeding or falling below a predetermined range of values;
   based on recognizing a critical event, retrieving a recommended treatment protocol for the patient from said database to address the critical event; and
   displaying said protocol on the second region of the display.

8. The method of claim 7, wherein the physiological parameter measuring devices comprise ECG, blood pressure, $SpO_2$, cardiac output, temperature, capnography, BIS, $SvO_2$ or EEG measuring devices.

9. The method of claim 7, wherein the database is remotely located.

10. The method of claim 7, wherein the patient data stored in the database includes patient health trends, lab data, event triggers, alarm history, clinical data, and treatment protocols.

11. The method of claim 7, wherein the display screen further comprises a plurality of data access buttons that can be actuated by a user to retrieve patient data.

12. The method of claim 7 further comprising, using the second region of display screen to launch applications for patient use, in an absence of a critical event.

13. A patient monitoring system having a patient mode and in a caregiver mode, the system comprising:
   a display screen connected to a plurality of physiological parameter measuring devices, said display screen comprising a first region for displaying real time physiological parameter data and a second region separate from the first region;
   a database comprising a memory for storing patient data; and
   a controller programmed to activate a caregiver mode in response to a critical event and a patient mode in an absence of a critical event, wherein the caregiver mode comprises retrieving patient data from said database and displaying said patient data on the second region of the display, and the patient mode comprises enabling the second region to launch applications for patient use wherein said applications in the patient mode include one or more of Internet programs, email programs, patient education software, entertainment software, or video conferencing applications and wherein in the patient mode the display screen comprises a plurality of widgets configured to be actuated by a user to launch said applications.

14. The system of claim 13 wherein the critical event is at least one of an alarm, a physiological parameter exceeding a predefined threshold, a passage of time, a physiological parameter falling below a predefined threshold, or a detected disconnection of a sensor.

15. The system of claim 13, wherein the patient data stored in the database includes patient health trends, lab data, event triggers, alarm history, clinical data, and treatment protocols.

16. The system of claim 13, wherein the display screen further comprises a plurality of data access buttons configured to be actuated by a user to retrieve patient data.

17. The system of claim 13, wherein the physiological parameter measuring devices comprise ECG, blood pressure, $SpO_2$, cardiac output, temperature, capnography, BIS, $SvO_2$ or EEG measuring devices.

18. The system of claim 13, wherein, in the caregiver mode, said display is configured to provide access to clinical settings.

* * * * *